(12) United States Patent
Sarkar et al.

(10) Patent No.: US 10,314,826 B2
(45) Date of Patent: Jun. 11, 2019

(54) METHODS OF TREATMENT OF ISCHEMIA-INDUCED ANGIOGENESIS AND ARTERIOGENESIS

(71) Applicants: Rajabrata Sarkar, Ellicott City, MD (US); Mark Hoofnagle, Baltimore, MD (US); Subhradip Mukhopadhyay, Baltimore, MD (US)

(72) Inventors: Rajabrata Sarkar, Ellicott City, MD (US); Mark Hoofnagle, Baltimore, MD (US); Subhradip Mukhopadhyay, Baltimore, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 243 days.

(21) Appl. No.: 14/617,149

(22) Filed: Feb. 9, 2015

(65) Prior Publication Data
US 2015/0224088 A1 Aug. 13, 2015

Related U.S. Application Data

(60) Provisional application No. 61/936,902, filed on Feb. 7, 2014.

(51) Int. Cl.
| | | |
|---|---|---|
| C07D 275/00 | (2006.01) | |
| A61K 31/428 | (2006.01) | |
| A61K 45/06 | (2006.01) | |

(52) U.S. Cl.
CPC ............ *A61K 31/428* (2013.01); *A61K 45/06* (2013.01)

(58) Field of Classification Search
CPC ..................................................... A61K 45/06
See application file for complete search history.

(56) References Cited

U.S. PATENT DOCUMENTS 7,012,087 B2    3/2006 Gudkov et al.

OTHER PUBLICATIONS

Jazayeri et al., Plast. Reconstr. Surg., 2008, 121:1135.*
Sohn et al., Cell Death and Differentiation, 2009, 16, 869-878.*
Kelly et al., J. Am. Soc. Nephrol., 2003, 14: 128-138.*
Hardcastle et al., J. Med. Chem. 2006, 49, 6209-6221, published on Sep. 28, 2006. (Year: 2006).*
Assadian, Sarah, et al., "P53 Inhibits Angiogenesis by Inducing the Production of Arresten", "Cancer Res", 2012, pp. 1270-1279, vol. 72, No. 5, Publisher: American Association for Cancer Research, Published in: DOI: 10.1158/0008-5472.
Dameron, K. M., et al., "The p53 Tumor Suppressor Gene Inhibits Angiogenesis by Stimulating the Production of Thrombospondin", "Cold Spring Harbor Symposia on Quantitative Biology", 1994, pp. 483-489, vol. LIX, Publisher: Cold Spring Harbor Laboratory Press, Published in: symposium.cshlp.org.
Giaccia, Amato J., and Michael B. Kastan, "The complexity of p53 modulation: emerging patterns from divergent signals", "Genes & Development", 1998, pp. 2973-2983, vol. 12, Publisher: Cold Spring Harbor Laboratory Press, Published in: www.genesdev.org.
Liu, Peitan, et al., "Pifithrin-alpha attenuates p53-mediated apoptosis and improves cardiac function in response to myocardial ischemia/reperfusion in aged rats", "Shock", 2006, pp. 608-614, vol. 26, No. 6, Publisher: The Shock Society, Published in: DOI: 10.1097/01.shk.0000232273.11225.af.
Morimoto, Yasutsugu, et al., "Atorvastatin Prevents Ischemic Limb Loss in Type 2 Diabetes: Role of p53", "J Atheroscler Thromb", 2011, pp. 200-208, vol. 18, No. 3, Publisher: Japan Atherosclerosis Society, Published in: https://www.jstage.jst.go.jp/article/jat/18/3/18_6437/_article.
Teodoro, Jose G., et al., "Inhibition of tumor angiogenesis by p53: a new role for the guardian of the genome", "J Molecular Medicine", 2007, pp. 1175-1186, vol. 85, Publisher: Springer-Verlag, Published in: DOI 10.1007/s00109-007-0221-2.
Zhang, Ying, et al., "Inhibition of p53 after acute myocardial infarction: Reduction of apoptosis is counteracted by disturbed scar formation and cardiac rupture", "J Molecular and Cellular Cardiology", 2011, pp. 471-478, vol. 50, Publisher: Elsevier, Published in: http://dx.doi.org/10.1016/j.yjmcc.2010.11.006.

* cited by examiner

*Primary Examiner* — Kaipeen E Yang
(74) *Attorney, Agent, or Firm* — Beusse Wolter Sanks & Maire

(57) ABSTRACT

It has now been discovered that p53 is a potent inhibitor of angiogenesis and arteriogenesis. Inhibition of p53 stimulates angiogenesis, arteriogenesis and improves perfusion in limbs. Therefore, methods are provided for treating diabetic-induced ischemia in a subject in need thereof comprising locally administering a therapeutically effective amount of one or more p53 molecule inhibitors or analogs and derivatives thereof to a site of ischemic tissue in the subject. Methods are provided for improving limb perfusion in a subject in need thereof comprising locally administering a therapeutically effective amount one or more p53 inhibitors together with a therapeutic agent or separately from the therapeutic agent to cells of a limb of a subject in need thereof. Methods are also provided for improving ischemia-induced angiogenesis and arteriogenesis in method of improving ischemia-induced angiogenesis in tissue of a limb comprising administering a therapeutically effective amount one or more p53 inhibitors individually or in combination with another therapeutic to a subject in need thereof.

27 Claims, 7 Drawing Sheets

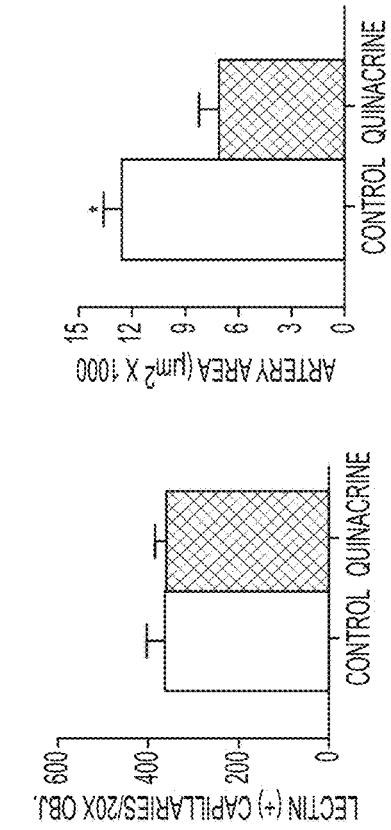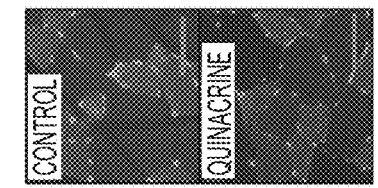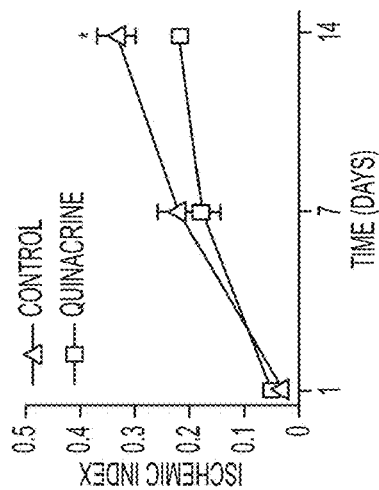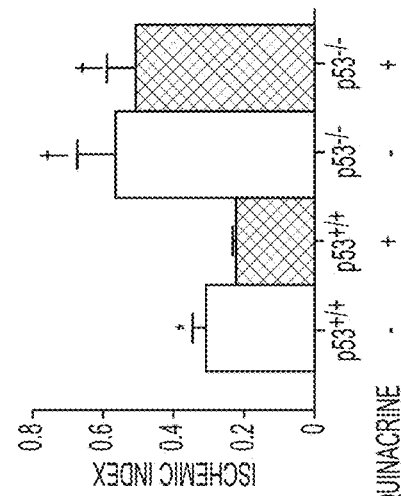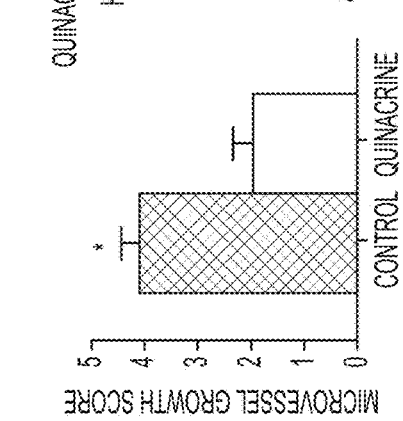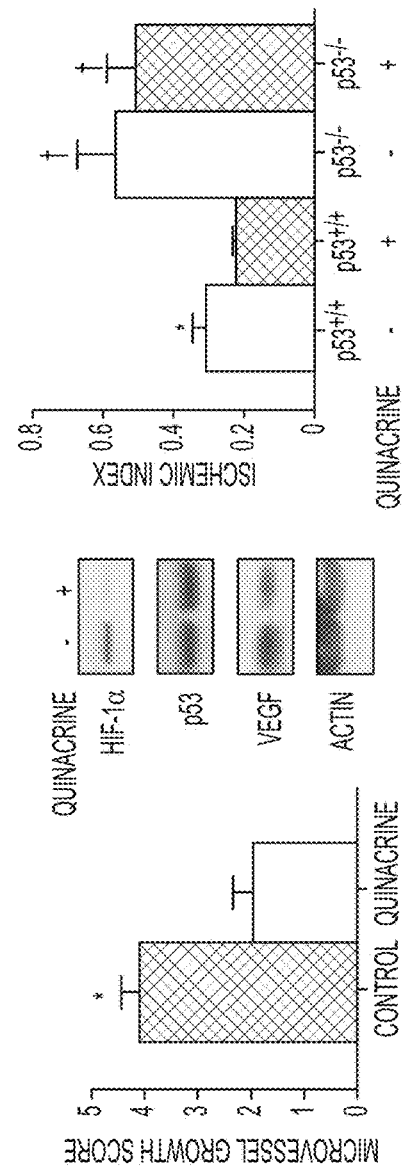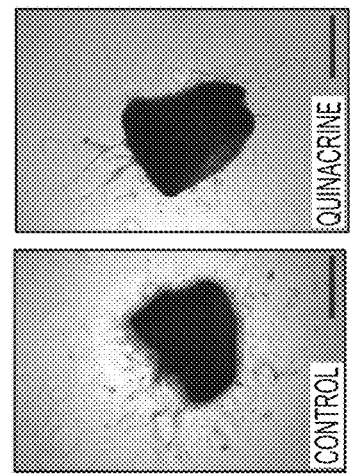
FIG. 4A
FIG. 4B
FIG. 4C
FIG. 4D
FIG. 4E
FIG. 4F

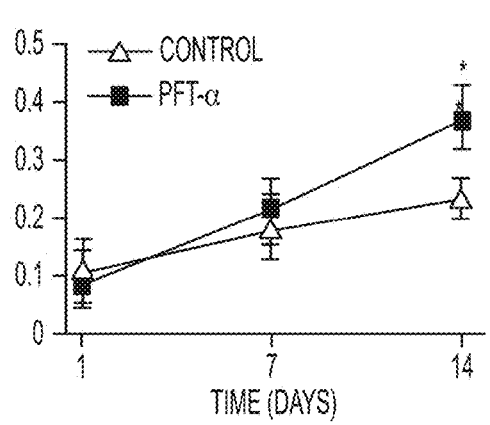
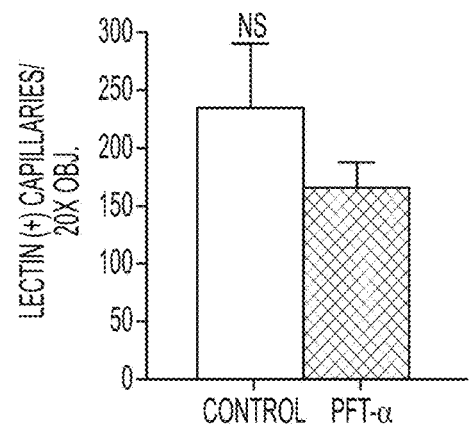
FIG. 5A
FIG. 5B
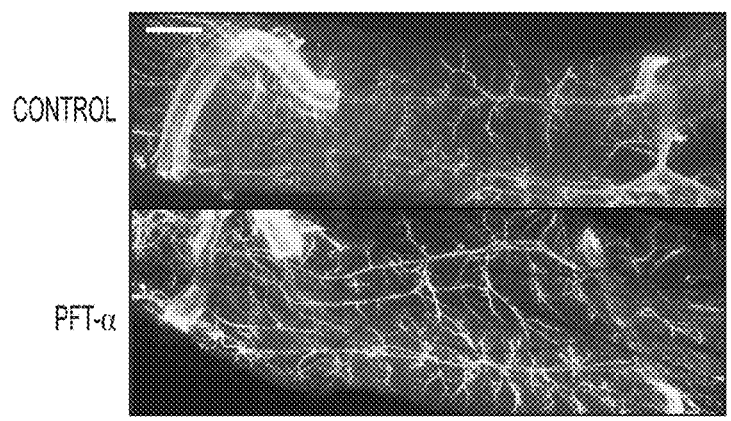
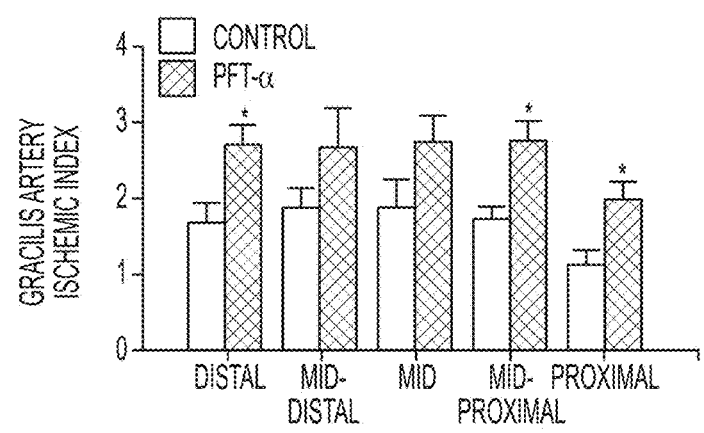
FIG. 5C

METHODS OF TREATMENT OF ISCHEMIA-INDUCED ANGIOGENESIS AND ARTERIOGENESIS

CROSS REFERENCE TO RELATED APPLICATIONS

This application claims the benefit of provisional application 61/936,902, entitled "Methods of Treatment of Ischemia-Induced Angiogenesis and Arteriogenesis," filed Feb. 7, 2014, the entire contents of which are incorporated herein.

STATEMENT OF GOVERNMENT INTEREST

This invention was made with government support under Grant Number HL080584 awarded by the National Institutes of Health. The government has certain rights in the invention.

BACKGROUND

Ischemic vascular disease is a major source of human morbidity and mortality, and more than half of all non-traumatic amputations in the United States occur in patients with diabetes—a major risk factor for peripheral vascular disease and amputation. Critical limb ischemia is estimated to develop in 500 to 1000 individuals per million per year. In the lower extremities, critical limb ischemia occurs when arteriogenesis is not adequate to overcome ischemia from arterial occlusive disease. In a large proportion of these patients, the anatomic extent and the distribution of arterial occlusive disease makes the patients unsuitable for operative or percutaneous revascularization. Despite advances in bypass surgery and endovascular intervention, more than 150,000 major amputations are performed in the United States due to critical limb ischemia. In other vascular beds, inadequate or maladaptive collateral artery formation leads to myocardial ischemia and infarction, stroke, mesenteric ischemia and ischemic nephropathy. Thus understanding the molecular mechanisms of collateral artery enlargement and vascular remodeling to develop new therapeutic strategies is a critical area of investigation.

Of particular interest, is the tumor suppressor protein p53. p53 is a highly conserved transcription factor involved in DNA repair, growth arrest, and apoptosis. p53 expression and activation increases in response to hypoxia, oxidative stress, and DNA damage. p53 regulates other forms of vascular remodeling, including atherosclerosis and intimal hyperplasia. The expression of p53 is increased by hindlimb ischemia and conditions associated with arterial occlusion such as diabetes and hypercholesterolemia independently induce p53 expression. Despite this substantial evidence suggesting that p53 may regulate ischemia-induced angiogenesis and arteriogenesis, the exact effect of this important stress-induced protein on these critical vascular responses to ischemia remains undefined. There is no optimal medical therapy for critical limb ischemia. Specifically, there is no pharmacological treatment for patients with tissue ischemia secondary to arterial occlusion to increase blood flow. Patients with arterial occlusive disease are treated with antiplatelet agents to prevent secondary platelet deposition, statins to prevent additional plaque buildup, and anticoagulants to prevent or treat secondary thrombosis. None of these classes of agents increase blood flow through augmentation of collateral artery enlargement and none have been shown to relieve ischemia.

In patients with tissue ischemia, because there is no pharmacological treatment, amputation, despite its associated morbidity, mortality, and functional implications, is often recommended as a solution to disabling symptoms. Therefore, it is desirable to develop novel therapies for treating of these patients. Here, the role of p53 in regulating ischemia-induced angiogenesis and arteriogenesis is defined. Potential mechanisms by which this regulation occurs in vivo has been identified. A direct negative effect of p53 on angiogenesis, arteriogenesis, and limb perfusion as well as several potential molecular mechanisms has been elucidated. It has been shown that pharmacologic modulation of p53 function improves collateral artery formation (arteriogenesis) and limb perfusion after ischemia, demonstrating the potential therapeutic benefit of inhibiting p53 to improve tissue perfusion in arterial occlusive disorders.

SUMMARY

It has been discovered that pharmacologic modulation of p53 function improves collateral artery formation (arteriogenesis) and limb perfusion after ischemia. The present invention is directed to methods of treating ischemia (i.e., diabetic-induced), improving angiogenesis, arteriogenesis, as well as limb perfusion, with the therapeutic use of p53 molecule inhibitors, analogs, and derivatives thereof. The small molecule inhibitor of p53, pifithrin alpha, was highly effective at increasing arteriogenesis and relieving ischemia in a clinically relevant diabetic ischemia model of hindlimb ischemia.

In certain embodiments, the p53 inhibitor or analogs and derivatives are locally administered alone to a site of ischemic tissue in a subject or in combination with systemic administration of one or more therapeutic agents. These therapeutic agents may be selected from but are not limited to the group consisting of: insulin; exenatide; liraglutide; pramlintide; sulfonylureas including glyburide, glimepiride, and glipizide; metformin; alpha-glucosidase inhibitors including acarbose, miglitol, and voglibose; and thiazolidinediones such as pioglitazone and rosiglitazone; alone or in some combination. Other therapeutic agents are selected from but not limited to the group consisting of: simvastatin; pravastatin; lovastatin; atorvastatin; niacin; rosuvastatin; pitavastatin; and fluvastatin; alone or in some combination.

In other aspects, in addition to one or more p53 molecule inhibitors or analogs and derivatives administered locally, one or more p53 molecule inhibitors or analogs and derivatives may be administered in combination orally, parenterally, sublingually, transdermally, rectally, transmucosally, or topically via a gel. Parenteral administration includes but is not limited to intravenous, intraarterial, intraperitoneal, intramuscular, intrathecal, and intraarticular administration. In certain embodiments, the p53 molecule inhibitors or analogs and derivatives thereof are administered in combination with a catheter delivery system to allow targeted delivery into a specific focal anatomic location or arterial bed. Or, the p53 molecule inhibitors or analogs and derivatives thereof are administered in combination with a topical gel to allow controlled release over a prolonged period of time. In certain embodiments, p53 molecule inhibitors are administered into surgical sites where tissue ischemia is a concern to allow localized arteriogenesis and to induce increased tissue perfusion in areas where it is known to be compromised preoperatively.

In certain embodiments, the p53 molecule inhibitors or analogs and derivatives thereof are administered in combination with a nanoparticle formulation to allow effective transmucosal absorption. In certain embodiments, the p53 molecule inhibitors or analogs and derivatives thereof are administered in combination with a nanoparticle formulation to allow more effective uptake into ischemic tissues. The p53 molecule inhibitors or analogs and derivatives thereof may also be administered alone or in conjunction with bypass surgery, endovascular surgery or endovascular revascularization. If administered orally, the p53 molecule inhibitors or analogs and derivatives thereof are administered in a dose of from about 25 mg to 250 mg.

In other embodiments, methods of improving limb perfusion in a subject in need thereof are provided by locally administering a therapeutically effective amount one or more p53 inhibitors together with a therapeutic agent or separately from the therapeutic agent to cells of a limb of a subject in need thereof.

In yet other aspects, methods of improving ischemia-induced angiogenesis in tissue of a limb are provided by administering a therapeutically effective amount one or more p53 inhibitors individually or in combination with another therapeutic to a subject in need thereof.

In certain embodiments, methods are also provided for improving ischemia-induced arteriogenesis in tissue of a limb comprising administering a therapeutically effective amount one or more p53 inhibitors individually or in combination with another therapeutic agent to a subject in need thereof.

These and other features, aspects, and advantages of the present invention will become better understood with regard to the following description, appended claims, and accompanying figures.

BRIEF DESCRIPTION OF THE DRAWINGS

The following drawings form part of the present specification and are included to further demonstrate certain embodiments of the present invention. The invention may be better understood by reference to one or more of these drawings in combination with the detailed description of specific embodiments presented herein.

FIG. 4A-4F are photographs and graphs illustrating pharmacological augmentation of p53 impairing angiogenesis and arteriogenesis after hindlimb ischemia.

FIG. 5A-5E are photographs and graphs illustrating pharmacological inhibition of p53 improves the arteriogenic response after hindlimb ischemia.

Figure 1A:
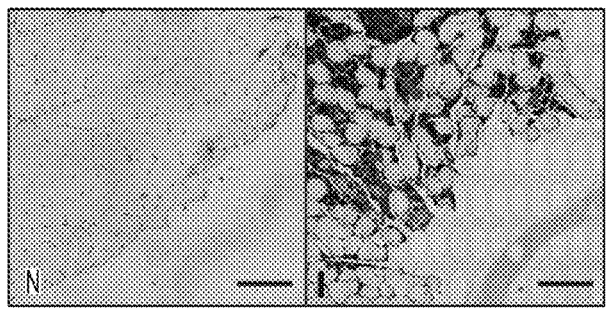
FIG. 1A-1F are photographs and graphs representing that loss of p53 potentiates angiogenesis and arteriogenesis following hindlimb ischemia.

In the Summary above, in the Detailed Description, and the claims below, as well as the accompanying figures, reference is made to particular features of the invention. It is to be understood that the disclosure of the invention in this specification includes all possible combinations of such particular features. For example, where a particular feature is disclosed in the context of a particular embodiment or embodiment of the invention, or a particular claim, that feature can also be used, to the extent possible, in combination with and/or in the context of other particular embodiments and embodiments of the invention, and in the invention generally. For the purposes of explanation, numerous specific details are set forth in order to provide a thorough understanding of the present invention. It will be apparent, however, to one skilled in the art that the present invention may be practiced without these specific details.

DETAILED DESCRIPTION

It has now been discovered that p53 is a potent inhibitor of angiogenesis and arteriogenesis. Inhibition of p53 stimulates angiogenesis, arteriogenesis, and improves perfusion in limbs. As a result, a novel therapeutic strategy using p53 inhibitors or analogs and derivatives thereof as a pharmacological treatment has been found and allows for the treatment of ischemic diseases (e.g., diabetes), particularly in subjects with critical limb ischemia.

In the following description, for the purposes of explanation, numerous specific details are set forth in order to provide a thorough understanding of the present invention. It will be apparent, however, to one skilled in the art that the present invention may be practiced without these specific details. In order that the invention may be readily understood and put into practical effect, particular preferred embodiments will now be described by way of the following non-limiting examples.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference.

Generally, nomenclatures used in connection with, and techniques of, cell and tissue culture, molecular biology, immunology, microbiology, genetics, protein, and nucleic acid chemistry and hybridization described herein are those well-known and commonly used in the art. The methods and techniques of the present invention are generally performed according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989); Ausubel et al., Current Protocols in Molecular Biology, Greene Publishing Associates (1992, and Supplements to 2002); Harlow and Lan, Antibodies: A Laboratory Manual, Cold Spring Harbor Laboratory Press, Cold Spring Harbor, N.Y. (1990); Principles of Neural Science, 4th ed., Eric R. Kandel, James H. Schwart, Thomas M. Jessell editors. McGraw-Hill/Appleton & Lange: New York, N.Y. (2000). Unless defined otherwise, all technical and scientific terms used herein have the same meaning as commonly understood by one of ordinary skill in the art.

The term "administering" as used herein, means a targeted structure-specific particulate delivery system may be administered or performed using any of the various methods or for delivering a biologically active agent.

The term "angiogenesis" as used herein, means a physiological process through which new blood vessels form from pre-existing vessels. Angiogenesis is a normal and vital process in growth and development, as well as in wound healing[1] and in the formation of granulation tissue.

The term "arteriogenesis" as used herein, means an increase in the diameter of existing arterial vessels to increase blood flow.

The terms "ischemia" or "ischemic," as used herein, mean insufficient blood flow or a restriction in blood supply therefore providing inadequate oxygenation to tissues. This causes a shortage of oxygen and glucose both of which are needed for cellular metabolism necessary to keep tissue alive. The most common causes of ischemia are progressive occlusion due to atherosclerotic plaque buildup which causes chronic narrowing (stenosis) of a supply artery. This narrowing can be followed by superimposed acute arterial thrombus formation. As blood flow is reduced to an organ, oxygen extraction increases. When the tissue is unable to extract adequate oxygen, the partial pressure of oxygen within the tissue fails (hypoxia) leading to a reduction in mitochondrial respiration and oxidative metabolism. Ischemia of the lower extremities causes pain with walking (claudication), then ulceration and gangrene leading to amputation. Ischemia of the heart causes angina, ischemic cardiomyopathy and acute myocardial infarction. Ischemia in other vascular territories can cause renal failure (ischemic nephropathy), intestinal angina and fatal bowel infarction (mesenteric ischemia) and vascular dementia and stroke (cerebrovascular ischemia).

The term "p53" or "tumor protein p53, cellular tumor antigen p53", "phosphoprotein p53", "tumor suppressor p53", "antigen NY-CO-13", or "transformation-related protein 53 (TRP53)", as used herein means is a protein that is encoded by the TP53 gene in humans. The p53 protein is crucial in multicellular organisms, where it regulates the cell cycle and, thus, functions as a tumor suppressor, preventing cancer. P53 is a transcription factor that in addition to activating apoptosis is a potent inhibitor of angiogenesis. P53 which is usually minimally expressed, is upregulated in tissues in diabetes. A "p53 molecule inhibitor," as used herein, means any compound that inhibits the expression of p53. P53 molecule inhibitors known in the art and commercially available include, but are not limited to JNJ-26854165 (serdemetan); pifithrin-α; NSC 207895; RITA (NSC 652287); Tenovin-1; Tenovin-6; NSC319726; pifithrin-µ; nutlin-3; roscovitine; and p-Nitro.

The term "pifithrin-α", or "pifithrin-alpha" as used herein is an inhibitor of p53, inhibiting p53-dependent transactivation of p53-responsive genes.

The terms "subject," "host," and "patient," as used herein, are used interchangeably and mean an animal being treated with the present compositions, including, but not limited to, simians, humans, avians, felines, canines, equines, rodents, bovines, porcines, ovines, caprines, mammalian farm animals, mammalian sport animals, and mammalian pets.

As used herein, a "therapeutic agent" means a compound or molecule capable of producing an effect. Preferably, the effect is beneficial.

As used herein, "therapeutically effective amount" means an amount sufficient to treat a subject afflicted with a disease (e.g., a diabetic disease) or to alleviate a symptom or a complication associated with the disease.

The term "treating" as used herein, means slowing, stopping or reversing the effects of a disease, particularly atherosclerosis, diabetic or coronary artery occlusive disease. As used herein, the terms "treatment," "treating," and the like, as used herein refer to obtaining a desired pharmacologic and/or physiologic effect. The effect may be prophylactic in terms of completely or partially preventing a condition or disease or symptom thereof and/or may be therapeutic in terms of a partial or complete cure for a condition or disease and/or adverse effect attributable to the condition or disease. "Treatment," includes any treatment of a condition or disease in a mammal, particularly in a human, and includes: (a) preventing the condition or disease or symptom thereof from occurring in a subject which may be predisposed to the condition or disease but has not yet been diagnosed as having it; (b) inhibiting the condition or disease or symptom thereof, such as, arresting its development; and (c) relieving, alleviating or ameliorating the condition or disease or symptom thereof, such as, for example, causing regression of the condition or disease or symptom thereof.

Overview

Ischemic vascular disease is a major source of human morbidity and mortality, and more than half of all non-traumatic amputations in the United States occur in patients with diabetes—a major risk factor for peripheral vascular disease and amputation. The tumor suppressor protein, p53, in addition to its role in regulating apoptosis, is a potent inhibitor of angiogenesis that functions by providing negative feedback on hypoxia-induced angiogenesis-inhibiting genes. In diabetes, p53 is upregulated in multiple cell types, increases endothelial progenitor cell senescence, and inhibits inflammation associated with improved wound-healing in diabetic animals. Loss of p53 results in improved response to ischemia in vivo. Therefore, in certain embodiments, inhibition of p53 using p53 inhibitors or analogs and derivatives thereof, improves the response to ischemia. Inhibition of p53 using pifithrin-α improves arteriogenesis, and limb profusion and allows for effecting treatment of diabetic-induced ischemia in subjects.

The critical process in restoring limb perfusion is arteriogenesis, or flow-mediated collateral artery enlargement around an arterial occlusion, rather than capillary angiogenesis [1, 30]. It was noted that all changes in limb perfusion with either genetic deletion or pharmacologic modulation of p53 correlated with arteriogenesis. Genetic deletion of p53 also increased capillary angiogenesis, but positive and negative modulation of p53 with quinacrine or PFT-α, respectively, altered limb perfusion and arteriogenesis without changes in capillary angiogenesis (FIG. 4B and FIG. 5). As genetic deletion of p53 causes complete loss of p53 activity whereas pharmacologic inhibition presumably does not, it was surmised that the effect of p53 on capillary angiogenesis requires total loss of p53 activity. The effect of p53 on arteriogenesis occurs with both total loss (genetic deletion) (FIG. 1) as well as the presumably partial inhibition by pharmacologic means (FIG. 5). Thus endogenous p53 regulates both arteriogenesis and angiogenesis, but the arteriogenic response is more sensitive to modulation of p53 activity and is also the critical factor for restoration of limb perfusion.

Background

Experimental hindlimb ischemia is associated with severe tissue hypoxia, necrosis, and cellular regeneration[28], each of which can activate p53 expression (For review, see ref. Gudkov and Komarova [29]). To ensure that the effects of p53 on collateral artery formation observed were not dependent on these specific pathological features, the effects of p53 gene deletion in the mouse mesenteric model of collateral artery enlargement, a well-established non-ischemic model for defining roles of individual genes in arteriogenesis [27] was studied. The effects of p53 deletion paralleled those noted in hindlimb ischemia, demonstrating p53 also negatively regulates collateral artery blood flow in a non-ischemic context.

Vascular remodeling that occurs in response to arterial occlusion is critical to determining the ultimate perfusion and fate of distal tissue. The normal circulatory response of the vasculature to arterial occlusion is enlargement of collateral arteries (arteriogenesis) to restore distal perfusion and relieve ischemia. Arterial occlusion creates a pressure gradient through pre-existing small muscular arteries around the blockage. This pressure gradient increases blood flow that causes vasodilation and subsequent structural enlargement to increase distal tissue perfusion [1]. Arterial occlusion also leads to downstream tissue hypoxia, activating hypoxia inducible factor-α (HIF-1α) [2] to increase expression of nitric oxide synthase [3], vascular endothelial growth factor (VEGF) [4], matrix metalloproteinases [5], and other genes involved in capillary angiogenesis and tissue remodeling [6].

Studies of statin treatment [24], semaphorin expression [16], and inhibition of retinal angiogenesis by p53 [26] indirectly suggest that endogenous p53 may regulate ischemia-induced angiogenesis, arteriogenesis, and limb perfusion. Despite this prior indirect evidence, the experimentation provided herein is the first to test the role of p53 in hindlimb ischemia using either targeted deletion of p53 gene or pharmacological modulation of p53.

Figure 3A:
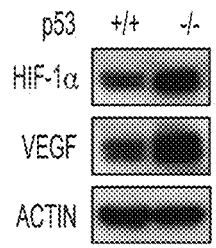
FIG. 3A-3D are photographs and bar graphs representing proangiogenic and anti-apoptotic effect of loss of p53.
Figure 3B:
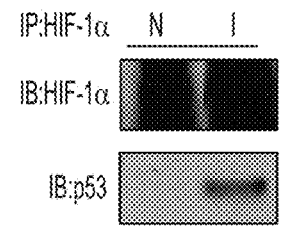
Figure 3C:
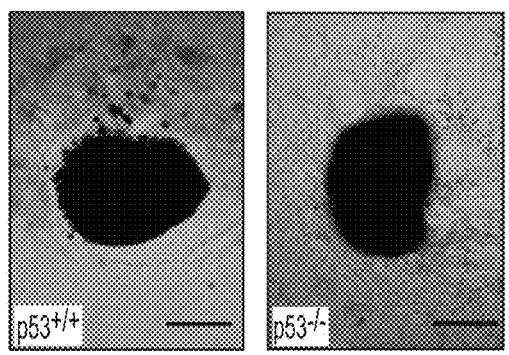

Vascular smooth muscle cell (VSMC) proliferation and migration are two necessary processes for positive arterial remodeling and collateral artery enlargement [30]. Inhibition of arteriogenesis by p53 is consistent with reports showing that p53 inhibits VSMC migration [31] and proliferation [26]. The effects of p53 on VSMC function have been characterized in the context of arterial injury, where p53 gene deletion resulted in increased cell proliferation, decreased apoptosis, and increased intimal lesions [21]. Although VSMC proliferation and migration are detrimental after arterial injury by contributing to neointimal hyperplasia, they are critical for arteriogenesis to increase collateral artery size and blood flow in order to relieve ischemia.

p53 inhibited angiogenesis and expression of HIF-1α and VEGF in vivo, and this may involve several mechanisms. Both p53 and HIF-1α are induced by hypoxia and several interactions between these two factors allow complex and reciprocal regulation (For review, see ref. Schmid et al. [32]). Ravi et al first reported that p53 binds and targets HIF-1α for degradation via the ubiquitin-proteosome pathway, which decreases HIF-1α-mediated VEGF expression and angiogenesis [20]. It was noted that ischemia-induced binding of p53 to HIF-1α, which is the first in vivo confirmation of this interaction. p53 can also be a transcriptional repressor of the VEGF gene [33] and also inhibits HIF-1α transcription by competing for p300 binding [32] or upregulation of the microRNA molecule miR-107 [34]. Conversely, HIF-1α has been shown to stabilize the p53 protein under hypoxic conditions [35]. HIF-1α and VEGF are well-characterized mediators of endothelial cell proliferation, migration, and capillary angiogenesis. A number of other mechanisms have been identified for regulation of angiogenesis by p53, including generation of anti-angiogenic collagen fragments via activation of prolyl hydroxylase [19] and expression of semaphorin 3E [16]. The increased angiogenesis noted with loss of p53 after ischemia in vivo (FIG. 1D) correlated with changes in HIF-1α and VEGF expression as did hypoxia-induced endothelial microvessel outgrowth from isolated aortic rings (FIG. 3C). The importance of the HIF-1α pathway in regulation of angiogenesis by p53 was demonstrated by the lack of effect of p53 activation on angiogenesis in animals lacking retinal HIF-1α [26].

Although overall limb perfusion after ischemia correlated with collateral artery enlargement rather than angiogenesis, the ability of p53 to regulate capillary angiogenesis is important in both positive and negative roles. Pharmacologic activation of p53 can inhibit pathologic retinal angiogenesis [26], and topical p53 gene silencing can enhance capillary angiogenesis during wound healing [25]. The effect of p53 on capillary angiogenesis appears to be highly context-specific, as p53 gene deletion increases ischemia-induced angiogenesis in skeletal muscle (FIG. 1D) but does not affect laser-induced retinal angiogenesis [26].

A recent report utilized p53 activation with the MDM2 inhibitor Nutlin-3 to inhibit pathologic retinal angiogenesis [26]. Nutlin-3 inhibited proliferation of both VSMC and endothelial cells, and induced apoptosis in endothelial cells. This correlated with the decreased apoptosis noted in vivo after ischemia in mice deficient in p53 (FIG. 3D) as well as the proposed effects of p53 on VSMCs in collateral arteries. We did not find a change in capillary angiogenesis with quinacrine activation of p53 whereas Chavala et al noted inhibition of angiogenesis with Nutlin-3; limb perfusion was not examined [26]. This difference may be due to the p53-independent effects of Nutlin-3, such as MDM2 binding to HIF-1α, as well as differences between quinacrine and Nutlin-3. Of note, the effects of Nutlin-3 on capillary angiogenesis were not repeated in p53-null mice, as was performed in our study with quinacrine (FIG. 4F) to confirm that the effects were mediated through a p53-dependent pathway.

Figure 3D:
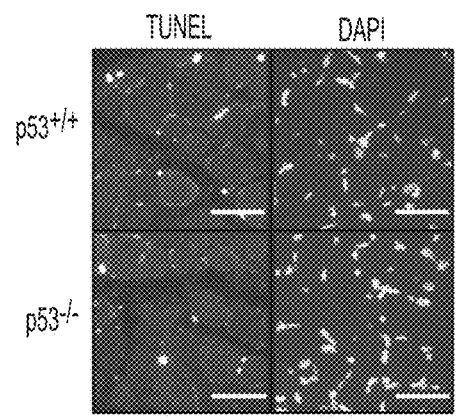

It was found that p53 gene deletion reduced cellular apoptosis in ischemic muscle (FIG. 3D). Similar regulation of apoptosis by p53 has been reported, particularly in cardiac tissue, where the effect of p53 on apoptosis appears to be the mechanism responsible for both post-infarct cardiac rupture as well the beneficial effect of p53 inhibition on post-infarct cardiac function [36,37,38]. We did not identify significant TUNEL-positive apoptosis in the non-ischemic more proximal portions of the limb where collateral artery enlargement takes place (data not shown). This suggests that the effect of p53 on arteriogenesis and limb perfusion is likely mediated by inhibition of VSMC migration and proliferation during arteriogenesis [26,31], rather than through changes in apoptosis.

Small molecule therapy targeting inhibition of p53 for occlusive vascular disease may be particularly effective in patients with diabetes, hypercholesterolemia, and other chronic cardiovascular conditions associated with increased oxidative stress, a well-known trigger for p53 expression. In this regard, it is interesting to speculate that the decreased collateral artery formation noted in diabetes [39] may be due to the increased p53 expression noted in this disease state [24], presumably due to increased oxidative stress. The limited proliferative and beneficial capacity of stem cells derived from patients with cardiovascular disease is well-documented, which negatively influences their therapeutic benefit for treatment of ischemic disease [40]. Inhibition of normal or elevated p53 expression in such patients may be more effective than proangiogenic therapies (angiogenic growth factors, stem cells, etc.), which depend on signaling pathways and regenerative capabilities that are known to be decreased in patients with atherosclerosis and cardiovascular disease.

In summary, the significant findings presented herein include: (i) endogenous p53 inhibits the angiogenic and arteriogenic responses to hindlimb ischemia as well as collateral arterial flow in a nonischemic mesenteric model, (ii) p53 inhibits ischemia-induced HIF-1α and VEGF expression and is induced by ischemia to directly bind HIF-1α, (iii) p53 inhibits hypoxia-induced endothelial cell growth and increases cellular apoptosis after ischemia, and (iv) positive and negative pharmacologic modulation of p53 reciprocally regulates limb perfusion, collateral arterial enlargement and expression of HIF-1α and VEGF protein. Collectively, these findings allowed for the identification of p53 as a negative regulator of ischemia-induced angiogenesis and arteriogenesis and characterizes p53 as a novel pharmacological target to improve tissue perfusion through augmented arteriogenesis after ischemia.

EMBODIMENTS

In certain embodiments, p53 molecule inhibitors or analogs and derivatives thereof in accordance with the present invention may be used to treat, alleviate, ameliorate, relieve, delay onset of, inhibit progression of, reduce severity of and/or reduce incidence of one or more symptoms or features of a disease, disorder, and/or condition.

A. Methods of Treating Diabetic-Induced Ischemia

The present invention discloses novel methods for the prevention and treatment (prophylactic and/or therapeutic) of diabetic-induced ischemia. In particular, certain embodiments relate to administering p53 inhibitors or analogs and derivatives thereof (e.g., pifithrin-α) locally to a site of ischemic tissue in a subject (i.e., a human limb). A derivative is a compound that is derived from a similar compound by some chemical or physical process. In the past it was also used to mean a compound that can be imagined to arise from another compound, if one atom is replaced with another atom or group of atoms, but modern chemical language now uses the term structural analogue for this meaning—thus eliminating ambiguity of both terms. The term "structural analogue" is common in organic chemistry. In biochemistry, the word is used for compounds that at least theoretically can be formed from the precursor compound. By "p53 inhibitor or analogs" as used herein is meant p53 inhibitors, both naturally occurring and synthetically produced, which through study of p53, would be expected to have an analogous inhibiting effect. Of course, similar to p53 inhibitors, the various chemical derivatives of this compound, such as other pharmaceutically acceptable derivatives, where appropriate, could be employed.

Other methods of local administration to the site of ischemic tissue in a subject include parenteral administration including intravenous drip, subcutaneous, intraperitoneal or intramuscular injection. In certain embodiments, the p53 inhibitor or analogs and derivatives thereof (e.g., pifithrin-α) is locally administered in combination with systemic administration of one or more therapeutic agents. In certain embodiments, the p53 inhibitor or analogs and derivatives thereof (e.g., pifithrin-α) is locally administered by perfusing the arteries supplying the ischemic tissue with an arterial perfusion catheter that is introduced from a remote site and directed with fluoroscopic guidance to the artery of interest. This catheter could contain a proximal occlusion balloon to transiently and temporarily inhibit native blood flow to allow a higher local concentration of the p53 inhibitor or analogs and derivatives thereof (e.g., pifithrin-α) to perfuse the tissue without washout from ongoing blood flow. Alternatively, in certain embodiments, the p53 inhibitor or analogs and derivatives thereof (e.g., pifithrin-α) is locally administered through either a side-hole catheter (for widespread dispersion with blood flow) or an end-hole catheter (for focal delivery in a small area with native blood flow).

Representative therapeutic agents are known in the art and are available commercially. They can include but are not limited to diabetic drugs and/or statin drugs. The therapeutic agent may be insulin; exenatide; liraglutide; pramlintide; sulfonylureas including glyburide, glimepiride, and glipizide; metformin; alpha-glucosidase inhibitors including acarboxe, miglitol, and voglibose; and thiazolidinediones such as pioglitazone and rosiglitazone; alone or in some combination. In certain embodiments, the therapeutic agent may be simvastatin; pravastatin; lovastatin; atorvastatin; niacin; rosuvastatin; pitavastatin; and fluvastatin; alone or in some combination. More than one therapeutic agent can be used concurrently, if desired.

p53 inhibitors or analogs and derivatives thereof (e.g., pifithrin-α) and therapeutic agent(s) are administered in a therapeutically effective amount (i.e., an amount that is sufficient to treat the disease, such as by ameliorating symptoms associated with the disease, preventing or delaying the onset of the disease, and/or also lessening the severity or frequency of symptoms of the disease). The amount which will be therapeutically effective in the treatment of a particular individual's disorder or condition will depend on the symptoms and severity of the disease, and can be determined by standard clinical techniques. In addition, in vitro or in vivo assays may optionally be employed to help identify optimal dosage ranges. The precise dose to be employed in the formulation will also depend on the route of administration, and the seriousness of the disease or disorder, and should be decided according to the judgment of a practitioner and each patient's circumstances. Effective doses may be extrapolated from dose-response curves derived from in vitro or animal model test systems.

B. Methods of Improving Limb Perfusion

In certain embodiments, methods are provided for improving limb perfusion in a subject by administering a therapeutically effective amount of a p53 inhibitor or analog and derivative thereof using an isolated limb perfusion circuit to achieve high local concentrations of these therapeutic agents. Isolated perfusion, as used herein, is the process of a body delivering blood to a capillary bed in its biological tissue. It is commonly used in human medicine for administration of therapeutic agents directly to an arm or leg, but in this case to promote angiogenesis and angiogenesis in a site of ischemia (e.g., the tissue of a human limb). It is also used in veterinary medicine to deliver drugs to a site of infection or injury, as well as for the treatment of cancer in dogs. In both cases, a tourniquet is used to temporarily reduce blood flow out of the area that is being treated. The flow of blood to and from the limb is temporarily stopped with a tourniquet, and therapeutic agents are put directly into the blood of the limb. This allows the person to receive a high dose of therapeutic agents in the area where the damage (i.e., ichemic tissue) has occurred. Blood flow through the limb is typically achieved using an extracorporeal circuit consisting of cannulae, tubing, peristaltic roller pump, heat exchanger, and pressure monitoring/safety devices.

C. Methods of Improving Ischemia-Induced Angiogenesis and Arteriogenesis

In other embodiments, methods are provided for improving ischemia-induced angiogenesis and methods for providing ischemia-induced arteriogenesis. It is known in the art that after birth, new blood vessel formation proceeds via angiogenesis or arteriogenesis. Angiogenesis (capillary sprouting) results in higher capillary density. Arteriogenesis (rapid proliferation of collateral arteries) is potentially able to significantly alter the outcome of coronary and peripheral artery disease. The processes share some growth features but differ in many aspects.

The term angiogenesis was introduced in 1935 by Hertig to describe the formation of new blood vessels in the placenta and, later, in 1971, by Folkman to describe the neovascularization accompanying the growth of solid tumors. Angiogenesis is a process by which new capillary blood vessels sprout from a preexisting blood vessel. It is an important component of various normal and pathological conditions such as wound healing, fracture repair, folliculogenesis, ovulation, and pregnancy. These periods of angiogenesis are tightly regulated. However, if not properly controlled, angiogenesis can also represent a significant pathogenic component of tumor growth and metastasis, rheumatic arthritis, and retinopathies. Angiogenesis is a complex phenomenon consisting of several distinct processes, which include endothelial migration and proliferation, extracellular proteolysis, endothelial differentiation (capillary tube formation), and vascular wall remodeling. It is important to recognize that these newly formed capillary tubes lack vascular smooth muscle cells. Any developing new network of endothelial tubes (sprouting capillaries) that is not surrounded by mural cells is fragile and prone to rupture, remains susceptible to hypoxic regulation, fails to become remodeled, and is unable to sustain proper circulation; it cannot adapt to changes in physiological demands of blood supply.

However, not every type of vascular growth results in capillary sprouting. In the case of chronic or acute occlusion of a major artery (coronary artery, femoral artery, etc.), preexisting arteriolar connections can be recruited to bypass the site of occlusion. This process, termed arteriogenesis, differs in many aspects from angiogenesis. Arteriogenesis is the rapid proliferation of preexisting collateral arteries. These vessels are thin-walled conduits that are composed of an endothelial lining, an internal elastic lamina, and one or two layers of smooth muscle cells. The presence of these native collaterals, which may not be utilized to provide perfusion under normal conditions, varies widely among species and also within individuals. However, these vessels have the ability to dramatically increase the lumen by growth so as to provide enhanced perfusion to the jeopardized ischemic regions. In case of chronic or acute occlusion of a major artery, collateral arteries can ameliorate the ensuing detrimental effects in many regions of the body (hindlimb, heart, brain, kidney). It is important to recognize that this process is not a passive dilatation but one of active proliferation and remodeling. Under normal flow conditions and depending on the pressure gradient between the interconnecting arterial networks there is only minimal net forward flow, but small amounts of flow may oscillate within the network.

Depending on the initial trigger, growth of blood vessels in adult organisms proceeds via two major processes, angiogenesis and arteriogenesis. While angiogenesis is induced by hypoxia and results in new capillaries, arteriogenesis is induced by physical forces, most importantly fluid shear stress. Consequently, chronically elevated fluid shear stress was found to be the strongest trigger under experimental conditions. Arteriogenesis describes the remodeling of preexisting arterio-arteriolar anastomoses to completely developed and functional arteries.

Arteriogenesis and angiogenesis differ rather fundamentally in that angiogenesis occurs in hypoxic tissue, which is usually far away from the localization of collateral vessels that bridge a major arterial occlusion, and takes place in a normoxic environment. The situation is clear in the vascular periphery, where occlusion of the femoral artery creates ischemia in the foot but collaterals develop in the thigh, a large distance indeed, defying any relation. It is true that under clinical circumstances, arteriogenesis is mostly closely associated with the occurrence of ischemia but causal relations usually do not exist. In fact, arteriogenesis may continue long after tissue ischemia has abated.

Collateral artery growth is the most important tissue saving, organ-saving, and often life-saving adaptive process after arterial occlusion in virtually all vascular provinces of the body. Arteriogenesis is the process whereby a preexisting arteriole from the resistance vessel class matures into an artery of the conductance vessel class, in contrast to angiogenesis, where a sprouting capillary originates from a preexisting capillary.

Therefore, in certain embodiments, p53 molecule inhibitors or analogs and derivatives thereof (e.g., pifithrin-$\alpha$) are administered in therapeutically effective amounts in tissue of a limb of a subject (e.g., human). The p53 molecule inhibitors or analogs and derivatives thereof may be administered individually or in combination with another therapeutic agent as described herein.

D. Routes of Administration and Dosage

Administration of p53 inhibitors or analogs and derivatives thereof alone or in combination with therapeutic agents of the present invention may be administered in a number of ways depending upon whether local or systemic treatment is desired and upon the area to be treated. Administration is preferably in a "therapeutically effective amount" this being sufficient to show effect or benefit to the subject. Administration may be, for example, daily, weekly or monthly. The actual amount administered, and rate, and time-course of administration, will depend on the nature and severity of what is being treated. It will also depend upon potential toxicity, overall health and age of the subject. Decisions on administration are within the responsibility of those of skill in the art.

In certain embodiments, p53 inhibitors or analogs and derivatives thereof are locally administered to a site of ischemic tissue in the subject. Preferably, administration may be accomplished via localized intra-arterial administration (are detailed above) or intramuscular administration directly into ischemic tissue. Other methods of local administration to the site of ischemic tissue in a subject include parenteral administration including intravenous drip, subcutaneous, intraperitoneal, intramuscular, intrarterial, intrathecal, and intraarticular injection.

In certain aspects, in addition to local administration of one or more p53 inhibitors or analogs or derivatives, these p53 inhibitors can also be administered systemically in combination with therapeutic agents orally, parenterally, sublingually, transdermally, vaginally, rectally, ophthalmic, subcutaneous, pulmonary, transmucosally, or topically via a gel. Administration can occur by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; 6,699,500 each of which is incorporated herein by reference. Such dosage forms can be used to provide slow or controlled release of one or more p53 inhibitors or analogs and derivatives and therapeutic agents using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled release formulations known to those of ordinary skill in the art, including those described herein, can be readily selected for use with p53 inhibitors and therapeutic agents of interest. Thus, the methods and formulations provided herein may encompass single unit dosage forms suitable for oral administration such as, but not limited to, tablets, capsules, gel caps, and caplets that are adapted for controlled release.

In certain embodiments, p53 molecule inhibitors or analogs and derivatives thereof are administered in combination with a topical gel to allow controlled release over a prolonged period of time or into surgical sites where tissue ischemia is of concern. All controlled release deliveries have a common goal of improving drug therapy over that achieved by their non-controlled counterparts. Ideally, the use of an optimally designed controlled release preparation in medical treatment is characterized by a minimum of drug substance being employed to cure or control the condition in a minimum amount of time. Advantages of controlled release formulations include extended activity of the drug, reduced dosage frequency, and increased subject compliance. In addition, controlled release formulations can be used to affect the time of onset of action or other characteristics, such as blood levels of the drug, and can thus affect the occurrence of side (e.g., adverse) effects.

Most controlled release formulations are designed to initially release an amount of drug and/or therapeutic agent that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled release of an active ingredient can be stimulated by various conditions including, but not limited to, pH, temperature, enzymes, water, or other physiological conditions or compounds.

In certain embodiments, p53 inhibitors or analogs and derivatives thereof alone or in combination with therapeutic agents may be administered using intravenous infusion, an implantable osmotic pump, a transdermal patch, liposomes, or other modes of administration. In one embodiment, a pump may be used (see, Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used. In yet another embodiment, a controlled release system can be placed in a subject at an appropriate site determined by a practitioner of skill, i.e., thus requiring only a fraction of the systemic dose (see, e.g., Goodson, Medical Applications of Controlled Release, vol. 2, pp. 115-138 (1984)). Other controlled release systems are discussed in the review by Langer (Science 249:1527-1533 (1990)). The p53 inhibitors or analogs and derivatives thereof and/or therapeutic agents can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of p53 inhibitor or analog and derivatives and/or therapeutic agents in such parenteral compositions is highly dependent on the specific nature thereof, as well as the needs of the subject.

The p53 inhibitors or analogs and derivatives thereof for systemic administration and/or therapeutic agents may be in the form of oral pharmaceutical dosage forms that can be either solid, gel or liquid and kits comprising them. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art. Such dosage forms contain predetermined amounts of active ingredients, and may be prepared by methods of pharmacy well known to those skilled in the art. See generally, Remington's Pharmaceutical Sciences, 20th ed., Mack Publishing, Easton Pa. (2000)

In certain embodiments, the oral pharmaceutical dosage forms are solid dosage forms, such as capsules or tablets. The tablets, pills, capsules, troches and the like can contain any of the following ingredients, or conjugates of a similar nature: a binder, a filler, a diluent; a disintegrating agent; a lubricant; a glidant; a sweetening agent; and a flavoring agent. Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, or from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL200, manufactured by W.R. Grace Co. of Baltimore, Md.), a coagulated aerosol of synthetic silica (marketed by Degussa Co. of Plano, Tex.), CAB-O-SM (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

Dosing is dependent upon severity and responsiveness of the condition to be treated, with course of treatment lasting from several days to several months or until a reduction of symptoms is achieved. One of skill in the art is knowledgeable about optimal dosing schedules as they can be calculated from measurements of accumulation in the body. Persons of ordinary skill in the art can easily determine optimum dosages, dosing methodologies and repetition rates. Therapeutically effective amounts (dosages) may vary depending on the relative potency of individual characteristics and can generally be routinely calculated based on molecular weight kand EC50s in in vitro and/or animal studies.

In certain embodiments, p53 molecule inhibitors or analogs and derivatives thereof such as pifithrin-α are formulated as an oral capsule containing about 75 mg, about 100 mg, about 250 mg, about 200 mg, about 225 mg, about 250 mg, about 300 mg, about 400 mg, about 500 mg or about 600 mg, about 700 mg or about 800 mg of the active ingredient. The capsule can contain inactive ingredients, such as polyethylene glycol 400, polysorbate 20, povidone, and butylated hydroxyanisole. The capsule shell can contain gelatin, sorbitol special glycerin blend and titanium dioxide.

E. Delivery

Catheter Delivery Systems

Systems that deliver p53 inhibitors or analogs and derivatives thereof and other therapeutic agents to a subject (e.g., targeted to a particular tissue or cell type or targeted to a specific diseased tissue but not normal tissue), or that control release of drugs has long been recognized as beneficial. For example, therapeutics that include an therapeutic agent and that are e.g., targeted to a particular tissue or cell type or targeted to a specific diseased tissue but not to normal tissue, may reduce the amount of the drug in tissues of the body that are not targeted. Effective drug targeting may reduce the undesirable and sometimes life threatening side effects common in disease therapy. In addition, such therapeutics may allow drugs to reach certain tissues they would otherwise be unable to reach.

In certain embodiments, administration of p53 inhibitors or analogs and derivatives thereof can be in combination with a catheter delivery system to allow targeted delivery into a specific focal anatomic location or arterial bed. In certain embodiments, the p53 inhibitor or analogs and derivatives thereof (e.g., pifithrin-α) is locally administered by perfusing the arteries supplying the ischemic tissue with an arterial perfusion catheter that is introduced from a remote site and directed with fluoroscopic guidance to the artery of interest. This catheter could contain a proximal occlusion balloon to transiently inhibit native blood flow to allow a higher local concentration of the p53 inhibitor or analogs and derivatives thereof (e.g., pifithrin-α) to perfuse the tissue without washout from ongoing blood flow. Alternatively, in certain embodiments, the p53 inhibitor or analogs and derivatives thereof (e.g., pifithrin-α) is locally administered through either a side-hole catheter (for widespread dispersion with blood flow) or an end-hole catheter (for focal delivery in a small area with native blood flow.

Catheter-based injections are less invasive and make it possible to evaluate cell products used as sole interventions. It is known in the art that two catheter-based methods have been used in clinical trials to deliver cells to the heart: direct intramyocardial injection and intracoronary infusion. Though substantially different techniques, they share the common goal of seeding progenitor cells into specific histoanatomic locations, specifically into the perivascular, interstitial space surrounding injured or ischemic myocardium.

In recent years various types of minute catheters have been developed for introduction into small body cavities and small vessels such as blood vessels in humans and animals. Often those minute catheters are very flexible and virtually lacking in rigidity. Furthermore, in many uses, the catheters are of great length and are extended along rather tortuous and extended paths within the body to reach desired locations. Naturally in order to limit the chances of injury to the patient and to allow it to be directed long distances by natural blood flow, it is desirable to have the most flexible and least rigid structure as possible for the member or catheter being introduced. This naturally presents various problems. For example once the rigidity is removed from the member, it is extremely difficult to advance the member into the vessel properly. For larger catheters, various guide wires and similar members have been utilized in the past for this purpose. More recently, attempts have been made to replace the guide wires which can only be used on the larger catheter, due to the size required for proper functioning, with a suitable method for the minute catheters. As a replacement, various fluid delivery systems have been developed as exemplified by U.S. Pat. Nos. 3,703,174; 3,826,256; 3,911,927; and 3,982,544.

Intravascularly-administrable, magnetically-localizable biodegradable microspheres containing a p53 inhibitor or analogs and derivatives thereof and/or therapeutic agent, can also be prepared and administered so that they can be permanently localized in a target capillary bed for release of the p53 inhibitor or analogs and derivatives thereof and/or therapeutic agent therein. The effects of the therapeutic agent can thereby be relatively confined to the area of the capillary bed.

In Conjunction with Bypass Surgery, Endovascular Surgery or Endovascular Revascularization.

In yet other aspects, methods are provided where the p53 molecule inhibitors or analogs and derivatives thereof are administered alone or in conjunction with bypass surgery, endovascular surgery or endovascular revascularization. Coronary artery bypass surgery, also known as coronary artery bypass graft (CABG, pronounced "cabbage") surgery, and colloquially heart bypass or bypass surgery, is a surgical procedure performed to relieve angina and reduce the risk of death from coronary artery disease. Arteries or veins from elsewhere in the patient's body are grafted to the coronary arteries to bypass atherosclerotic narrowings and improve the blood supply to the myocardium (heart muscle). This surgery is usually performed with the heart stopped, necessitating the usage of cardiopulmonary bypass; techniques are available to perform CABG on a beating heart, so-called "off-pump" surgery.

Endovascular surgery is a form of minimally invasive surgery that was designed to access many regions of the body via major blood vessels. Endovascular techniques were originally pioneered for diagnostic purposes by radiologists. Basic techniques involve the introduction of a catheter percutaneously into a large blood vessel (Seldinger technique). Typically the blood vessel chosen is the femoral artery or a vein found near the groin. Access to the femoral artery for example, is required for coronary, carotid, and cerebral angiographic procedures. The catheter is injected with a radio-opaque dye that can be seen on live X-ray or fluoroscopy. As the dye courses through the blood vessels, characteristic images are seen by experienced viewers and can assist in the diagnosis of diseases such as atherosclerosis, vascular trauma, or aneurysms.

If a subject is suffering from lower extremity peripheral artery disease (PAD), there endovascular revascularization that can relieve symptoms. Performed under local anesthesia, vascular and endovascular surgeons perform endovascular revascularization to clear blockages in the arteries and remove the plaque that is causing decreased blood flow. This alleviates the pain and stops the tissue decay/loss associated with lower extremity PAD. This procedure is suitable for nonsurgical candidates, is faster than a bypass and results in faster recovery, with most people feeling better instantly and able to resume all normal activities within a few days.

In Combination with Nanoparticle Formulations

In certain embodiments, the p53 molecule inhibitors or analogs and derivatives thereof and/or therapeutic agents are administered in combination with a nanoparticle formulation to allow effective absorption and more effective uptake into ischemic tissues. Therapeutics that offer controlled release and/or targeted therapy also must be able to deliver an effective amount of therapeutic agent, which is a known limitation in other nanoparticle delivery systems. For example, it can be a challenge to prepare nanoparticle systems that have an appropriate amount of drug associated each nanoparticle, while keeping the size of the nanoparticles small enough to have advantageous delivery properties. However, while it is desirable to load a nanoparticle with a high quantity of therapeutic agent, nanoparticle preparations that use a drug load that is too high will result in nanoparticles that are too large for practical therapeutic use.

Nanoparticle formulations may include polymeric nanoparticles that include p53 molecule inhibitor or analogs and derivatives thereof and/or a therapeutic agent. In general, a "nanoparticle" refers to any particle having a diameter of less than 1000 nm, e.g. about 10 nm to about 200 nm. Disclosed therapeutic nanoparticles may include nanoparticles having a diameter of about 60 to about 120 nm, or about 70 to about 130 nm, or about 60 to about 140 nm. Nanoparticles disclosed herein include one, two, three or more biocompatible and/or biodegradable polymers. For example, a contemplated nanoparticle may include about 10 to about 99 weight percent of a one or more block copolymers that include a biodegradable polymer and polyethylene glycol, and about 0 to about 50 weight percent of a biodegradable homopolymer.

In one embodiment, disclosed nanoparticle formulations may include a targeting ligand, e.g., a low-molecular weight PSMA ligand effective for the treatment of a disease or disorder, such as diabetes and/or cardiovascular disease in a subject in need thereof. In certain embodiments, the low-molecular weight ligand is conjugated to a polymer, and the nanoparticle comprises a certain ratio of ligand-conjugated polymer (e.g., PLA-PEG-Ligand) to non-functionalized polymer (e.g. PLA-PEG or PLGA-PEG). The nanoparticle can have an optimized ratio of these two polymers such that an effective amount of ligand is associated with the nanoparticle for treatment of a disease or disorder, such as cancer. For example, an increased ligand density may increase target binding (cell binding/target uptake), making the nanoparticle "target specific." In another embodiment, disclosed nanoparticle formulations may include a poly-L-glycolic acid (PLGA) formulation which has been shown to have preferential uptake in ischemic cells.

Alternatively, a certain concentration of non-functionalized polymer (e.g., non-functionalized PLGA-PEG copolymer) in the nanoparticle can control inflammation and/or immunogenicity (i.e., the ability to provoke an immune response), and allow the nanoparticle to have a circulation half-life that is adequate for the treatment of a disease or disorder (e.g., diabetes, heart disease, and cancer). Furthermore, the non-functionalized polymer may, in some embodiments, lower the rate of clearance from the circulatory system via the reticuloendothelial system (RES). Thus, the non-functionalized polymer may provide the nanoparticle with characteristics that may allow the particle to travel through the body upon administration. In some embodiments, a non-functionalized polymer may balance an otherwise high concentration of ligands, which can otherwise accelerate clearance by the subject, resulting in less delivery to the target cells.

For example, disclosed herein are nanoparticle formulations having nanoparticles that may include functionalized polymers conjugated to a ligand that constitute approximately 0.1-50, e.g., 0.1-30, e.g., 0.1-20, e.g., 0.1-10 mole percent of the entire polymer composition of the nanoparticle (i.e., functionalized+non-functionalized polymer). Also disclosed herein, in another embodiment, are nanoparticles that include a polymer conjugated (e.g., covalently with (i.e. through a linker (e.g. an alkylene linker) or a bond) with one or more low-molecular weight ligands, wherein the weight percent low-molecular weight ligand with respect to total polymer is between about 0.001 and 5, e.g., between about 0.001 and 2, e.g., between about 0.001 and 1.

Also provided herein are polymeric nanoparticles that include about 2 about 20 weight percent active agent. For example, a composition comprising such nanoparticles may be capable of delivering an effective amount to e.g. a target body area of a patient. For example, disclosed nanoparticles may be able to efficiently bind to or otherwise associate with a biological entity, for example, a particular membrane component or cell surface receptor. Targeting of a therapeutic agent (e.g., to a particular tissue or cell type, to a specific diseased tissue but not to normal tissue, etc.) is desirable for the treatment of tissue specific diseases such diabetes and cardiovascular disease. Additionally, disclosed nanoparticles may allow for the administration of a lower dose of the therapeutic agent (as compared to an effective amount of agent administered without disclosed nanoparticles or formulations) which may reduce the undesirable side effects.

In some embodiments, the nanoparticles of the invention comprise a matrix of polymers and a therapeutic agent. In some embodiments, a therapeutic agent and/or targeting moiety (i.e., a low-molecular weight PSMA ligand) can be associated with at least part of the polymeric matrix. For example, in some embodiments, a targeting moiety (e.g. ligand) can be covalently associated with the surface of a polymeric matrix. In some embodiments, covalent association is mediated by a linker. The therapeutic agent can be associated with the surface of, encapsulated within, surrounded by, and/or dispersed throughout the polymeric matrix. A wide variety of polymers and methods for forming particles therefrom are known in the art of drug delivery. In some embodiments, the disclosure is directed toward nanoparticles with at least two macromolecules, wherein the first macromolecule comprises a first polymer bound to a low-molecular weight ligand (e.g. targeting moiety); and the second macromolecule comprising a second polymer that is not bound to a targeting moiety. The nanoparticle can optionally include one or more additional, unfunctionalized, polymers.

Any polymer can be used in accordance with the present invention. Polymers can be natural or unnatural (synthetic) polymers. Polymers can be homopolymers or copolymers comprising two or more monomers. In terms of sequence, copolymers can be random, block, or comprise a combination of random and block sequences. Typically, polymers in accordance with the present invention are organic polymers. The term "polymer," as used herein, is given its ordinary meaning as used in the art, i.e., a molecular structure comprising one or more repeat units (monomers), connected by covalent bonds. The repeat units may all be identical, or in some cases, there may be more than one type of repeat unit present within the polymer. In some cases, the polymer can be biologically derived, i.e., a biopolymer. Non-limiting examples include peptides or proteins. In some cases, additional moieties may also be present in the polymer, for example biological moieties such as those described below. If more than one type of repeat unit is present within the polymer, then the polymer is said to be a "copolymer." It is to be understood that in any embodiment employing a polymer, the polymer being employed may be a copolymer in some cases. The repeat units forming the copolymer may be arranged in any fashion. For example, the repeat units may be arranged in a random order, in an alternating order, or as a block copolymer, i.e., comprising one or more regions each comprising a first repeat unit (e.g., a first block), and one or more regions each comprising a second repeat unit (e.g., a second block), etc. Block copolymers may have two (a diblock copolymer), three (a triblock copolymer), or more numbers of distinct blocks.

Disclosed nanoparticles may have a substantially spherical (i.e., the particles generally appear to be spherical), or nonspherical configuration. For instance, the particles, upon swelling or shrinkage, may adopt a non-spherical configuration. In some cases, the particles may include polymeric blends. For instance, a polymer blend may be formed that includes a first polymer comprising a targeting moiety (i.e., a low-molecular weight PSMA ligand) and a biocompatible polymer, and a second polymer comprising a biocompatible polymer but not comprising the targeting moiety. By controlling the ratio of the first and second polymers in the final polymer, the concentration and location of targeting moiety in the final polymer may be readily controlled to any suitable degree.

Disclosed nanoparticles may have a characteristic dimension of less than about 1 micrometer, where the characteristic dimension of a particle is the diameter of a perfect sphere having the same volume as the particle. For example, the particle can have a characteristic dimension of the particle can be less than about 300 nm, less than about 200 nm, less than about 150 nm, less than about 100 nm, less than about 50 nm, less than about 30 nm, less than about 10 nm, less than about 3 nm, or less than about 1 nm in some cases. In particular embodiments, the nanoparticle of the present invention has a diameter of about 80 nm-200 nm, about 60 nm to about 150 nm, or about 70 nm to about 200 nm.

In one set of embodiments, the particles can have an interior and a surface, where the surface has a composition different from the interior, i.e., there may be at least one compound present in the interior but not present on the surface (or vice versa), and/or at least one compound is present in the interior and on the surface at differing concentrations. For example, in one embodiment, a compound, such as a targeting moiety (i.e., a low-molecular weight ligand) of a polymeric conjugate of the present invention, may be present in both the interior and the surface of the particle, but at a higher concentration on the surface than in the interior of the particle, although in some cases, the concentration in the interior of the particle may be essentially nonzero, i.e., there is a detectable amount of the compound present in the interior of the particle.

In some cases, the interior of the particle is more hydrophobic than the surface of the particle. For instance, the interior of the particle may be relatively hydrophobic with respect to the surface of the particle, and a drug or other payload may be hydrophobic, and readily associates with the relatively hydrophobic center of the particle. The drug or other payload can thus be contained within the interior of the particle, which can shelter it from the external environment surrounding the particle (or vice versa). For instance, a drug or other payload contained within a particle administered to a subject will be protected from a subject's body, and the body will also be isolated from the drug. Yet another aspect of the invention is directed to polymer particles having more than one polymer or macromolecule present, and libraries involving such polymers or macromolecules. For example, in one set of embodiments, particles may contain more than one distinguishable polymers (e.g., copolymers, e.g., block copolymers), and the ratios of the two (or more) polymers may be independently controlled, which allows for the control of properties of the particle. For instance, a first polymer may be a polymeric conjugate comprising a targeting moiety and a biocompatible portion, and a second polymer may comprise a biocompatible portion but not contain the targeting moiety, or the second polymer may contain a distinguishable biocompatible portion from the first polymer. Control of the amounts of these polymers within the polymeric particle may thus be used to control various physical, biological, or chemical properties of the particle, for instance, the size of the particle (e.g., by varying the molecular weights of one or both polymers), the surface charge (e.g., by controlling the ratios of the polymers if the polymers have different charges or terminal groups), the surface hydrophilicity (e.g., if the polymers have different molecular weights and/or hydrophilicities), the surface density of the targeting moiety (e.g., by controlling the ratios of the two or more polymers).

EXAMPLES

The invention is illustrated herein by the experiments described by the following examples, which should not be construed as limiting. The contents of all references, pending patent applications and published patents, cited throughout this application are hereby expressly incorporated by reference. Those skilled in the art will understand that this invention may be embodied in many different forms and should not be construed as limited to the embodiments set forth herein. Rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

Example 1: Materials and Methods

Animal Surgical Models

Figure 2A:
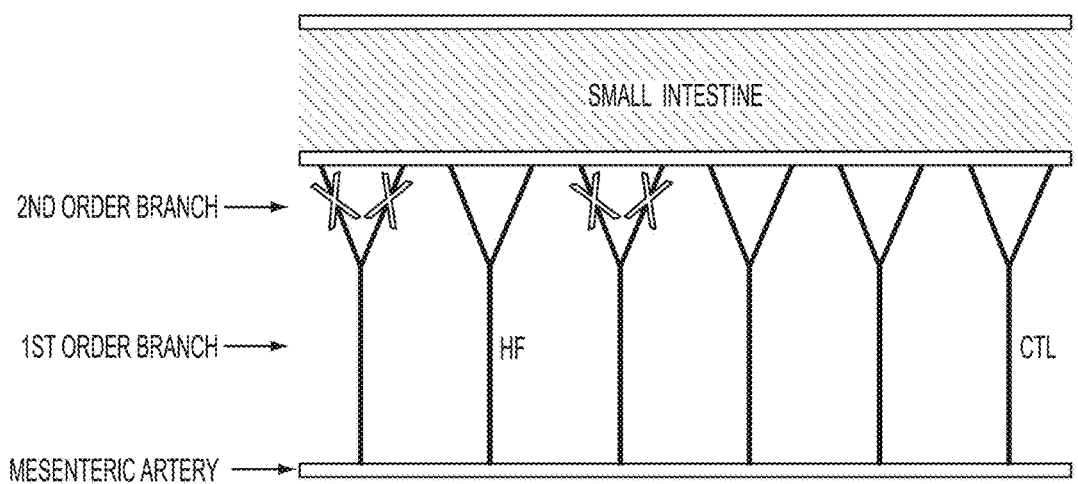
FIG. 2A-2D are graphs and photographs illustrating that loss of p53 improves the arteriogenic response after mesenteric artery ligation.

All experiments and animal husbandry were performed with approval from the University of California, San Francisco and University of Maryland Institutional Animal Care and Use Committees. Wild-type ($p53^{+/+}$), p53-null ($p53^{-/-}$), and $p53^{-/+}$ heterozygoytes were maintained on a C57Bl/6 background. Hindlimb ischemia was surgically induced in 8- to 12-week old male mice by excision of the unilateral femoral artery under isofluorane anesthesia as previously described [5]. For pharmacological modulation of p53 in vivo, quinacrine or vehicle (sterile water) was administered intraperitoneally at 10 mg/kg/day, beginning 5 days prior to surgery, and continued daily post-operatively until the experimental endpoint; PFT-α or vehicle (10% DMSO) was administered intraperitoneally at 2 mg/kg/day every other day beginning two days prior to surgery and continued until the experimental end-point. Mesenteric artery ligation was performed on 8- to 12-week old male wild-type and $p53^{-/-}$ mice as described previously with modifications [27]. A laparotomy was performed and the small intestine exposed and suffused with warmed saline. A $2^{nd}$ order straight artery branching off of the superior mesenteric artery was chosen as a high flow collateral vessel (HF), after which the arteries immediately bordering it were skeletonized and ligated with 6-0 silk thread (FIG. 2A). The control artery (CTL) was considered a straight artery three arteries from the site of ligation. The peritoneum and skin were closed individually with 4-0 absorbable sutures.

Blood Flow Determination

Restoration of blood flow after hindlimb ischemia was assessed by laser Doppler perfusion imaging (LDPI) of the hindlimb paws using a PeriScan PIM 3 System (Perimed AB; Stockholm, Sweden) as previously described [5]. Three successive readings were averaged and expressed as an ischemic index (ischemic paw over contralateral paw). For mesenteric artery ligation, blood flow was measured in the HF or CTL artery as volume-flow with a nanoprobe secured around the artery (0.5 mm nanoprobe, Transonic Systems Inc., Ithaca, N.Y.) in anesthetized mice. Flow was averaged over ten minutes and expressed as an arterial index (HF artery over CTL artery).

Histology p53 expression (tibialis anterior; TA) and larger blood vessels in the thigh adductor muscles were identified by immunostaining with antibodies specific to p53 (Santa Cruz Biotechnology) and α-smooth muscle actin (α-sma) (Novus Biologicals; Littleton, Colo.), respectively, and visualized using the Vector ABC kit and VIP substrate (Vector Labs; Burlingame, Calif.). For capillary density analysis, fixed TA muscles were frozen in an isopentane/liquid nitrogen bath, subjected to a sucrose gradient for cryoprotection, embedded in O.C.T., and cut into 5 μm frozen sections. Sections were washed briefly in Phosphate Buffered Saline (PBS) containing 0.05% Tween 20 (PBS-T), blocked for 1 hour at room temperature in PBS containing 5% BSA, and incubated with fluoresceinated isolectin B4 (lectin) (Vector). TUNEL analysis was performed on paraffin-embedded TA muscles using the ApopTag kit (Millipore; Temecula, Calif.). For capillary and TUNEL analysis, images were taken from two 5 μm thick sections, 1 mm apart, from each ischemic muscle in three randomly chosen fields of three areas. To study the arteriogenic response, two α-sma positive collateral arteries identified as being present in all animals were selected for analysis. Two areas were studied 1 mm apart with two 5 μm sections per area and the results averaged.

Independent experiments with separate animal cohorts for capillary and larger artery analysis were performed. For the gracilis arteriogenesis assay, animals were euthanized and fixed perfused with 10 ml PBS containing Heparin 100 U/L, sodium nitroprusside 10 um (Sigma Aldrich, St. Louis, Mo.), and adenosine 100 μm (Sigma), followed by 10% neutral-buffered formalin (Sigma), and PBS containing glycine 100 mM (Sigma) at 37° C., The gracilis muscle was harvested and solubilized in PBS containing 0.5% triton and 1% BSA for 24 hours, then incubated with α-sma-cy3 antibody (Sigma) at a concentration of 1:250 in 0.1% triton (Sigma) in PBS for 48 hours. The muscle was then dehydrated by successive one hour immersions in 50%, 70%, 90%, 95% and 100% ethanol, followed by clearing in a 1:1 solution of benzyl alcohol/benzyl benzoate (Sigma) prior to mounting and imaging. Vascular regions were quantified individually and normalized to the contralateral control muscle. For mesenteric artery visualization, animals were perfused with lectin (Vector) prior to fixation, followed by perfusion with Microfil (Flow Tech Inc.; Carver, Mass.). The HF and CTL artery were excised and the arteries embedded in OCT. Two 5 μm sections in two separate areas 0.5 mm apart were measured and the results averaged. All analyses were performed using the National Institute for Health imaging software, ImageJ (http://rsbweb.nih.gov/ij/).

Immunoblotting

TA tissue from ischemic and control limbs from were harvested and pulverized in liquid nitrogen. For whole cell lysates, pulverized tissue was incubated in a modified RIPA buffer (50 mM Tris-HCl, pH 7.4; 1% SDS; 1% NP-40; 0.25% sodium deoxycholate; 1 mM PMSF; 1 mM DTT; Complete Mini, EDTA-free protease inhibitor cocktail and PhosStop phosphatase inhibitor tablets (Roche Applied Science; Indianapolis, Ind.), strained, and sonicated 3 times for 10 seconds. Samples were centrifuged at 10,000 G for ten minutes at 4 C, and the supernatant preserved. Protein concentration was measured using a BCA Protein Assay Kit. A total of 20 μg of protein was resolved on a 4-12% Bis-Tris gradiant polyacrylamide gel (Invitrogen; Carlsbad, Calif.)

under reduced conditions and transferred to a PVDF membrane (Amersham Biosciences; Pittsburgh, Pa.). Membranes were blocked for 30 minutes at room temperature in StartingBlock blocking buffer (Pierce; Rockford, Ill.) and incubated with antibodies specific to actin, VEGF, p53, and tubulin (Santa Cruz Biotechnology; Santa Cruz, Calif.), or HIF-1α (Novus Biologicals; Littleton, CO5). Protein expression was visualized by chemiluminescence using ECL Plus (Amersham) on medical x-ray film.

Co-Immunoprecipitation

Tissue from ischemic and control limbs were harvested, pulverized in liquid nitrogen, lysed in extraction buffer with a series of sucrose concentrations (2 mM EDTA; 2.5 mM DTT; 10 mM HEPES, pH 8; and 0.25/0.4/1.4 M sucrose, respectively), strained through a 70 μm cell strainer, centrifuged at 4,000 Gs for 10 minutes at 4° C. and the fractions taken for analysis. Samples were pre-cleared with A/G-Plus agarose beads (Pierce), probed with an HIF-1α-specific antibody overnight at 4° C., and followed by incubation with A/G-agarose beads for three hours at 4° C. Samples were washed repeatedly in PBS-T. The p53 protein bound to the beads was detected by immunoblotting as described above. Nonimmune IgG-treated samples served as a control.

Endothelial Outgrowth Aortic Ring Assay

Aortic rings (1 mm thick from the descending thoracic mouse aorta) were placed on a layer of solidified Matrigel (BD Bioscience; San Jose, Calif.) in 48-well plates and embedded with additional Matrigel. Mineral oil (Sigma) overlay was applied to achieve a hypoxic environment and mineral oil-free samples were used as the normoxic control. All samples were incubated at 37° C. in a humidified atmosphere of 5% $CO_2$ for up to 2 weeks. Media (MCDB 131, 10% FBS, 14 mM $NaHCO_3$, and 1% Penicillin and Streptavidin) and mineral oil were replenished twice weekly. 20 μM quinacrine or PBS-vehicle control were added to the media. Growth scores were performed using a 5-point scale by two independent, blinded reviewers and results from both graders were averaged used for comparison.

Statistical Analysis

Statistical analysis was performed using Microsoft Excel (Version 14.0.0, Microsoft Office 2011, Microsoft; Redmond, Wash.) and SPSS Statistics (Version 19, IBM; Armonk, N.Y.). Results were expressed as the mean±standard error of the mean (s.e.m.). A two-tailed student's t test or analysis of variance was performed for statistical comparison and an observed P value of 0.05 or less was considered statistically significant.

Figure 1B:
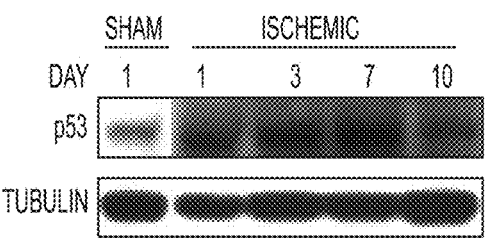
Figure 1C:
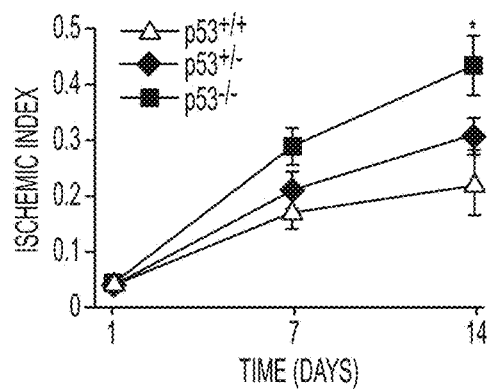
Figure 1D:
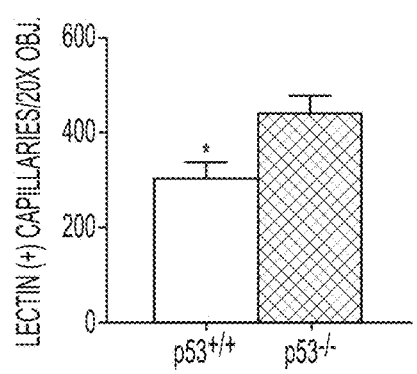

Example 2: p53 is Upregulated in Ischemic Tissue Following Hindlimb Ischemia and Negatively Regulates Ischemia-Induced Angiogenesis and Arteriogenesis It was confirmed that p53 expression increased following hindlimb ischemia. p53 protein was detected in the interstitial spaces of ischemic hindlimb muscle tissue three days following hindlimb ischemia (FIG. 1A) and p53 protein levels were robustly expressed up to 7 days in ischemic tissue (FIG. 1B). FIG. 1A is a photograph of p53 protein (black arrows) showing detection in ischemic tissue 3 days after hindlimb ischemia. FIG. 1B is a photograph illustrating an increase in p53 protein expression in ischemic muscle tissue up to 1 week following hindlimb ischemia. Analysis of blood flow after ischemia revealed that $p53^{-/-}$ mice had enhanced restoration of blood flow at 2 weeks compared to $p53^{+/+}$ mice, with an intermediate response observed in heterozygous $p53^{+/-}$ mice (FIG. 1C). FIG. 1C is a graph that illustrates showing marked improvement in blood flow restoration in $p53^{-/-}$ mice compared to $p53^{+/+}$ mice. Compared to wildtype $p53^{+/+}$ mice, $p53^{-/-}$ mice demonstrated a significant increase in both capillary density (FIG. 1D) and collateral artery development (FIG. 1E and FIG. 1F) at 2 weeks after hindlimb ischemia. FIG. 1D includes a photograph and bar graph illustrating increased capillary density in $p53^{-/-}$ mice.

Figure 1E:
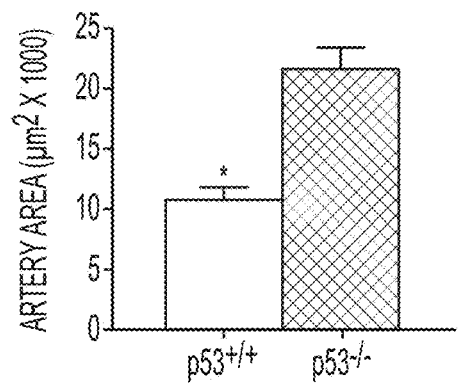
Figure 1F:
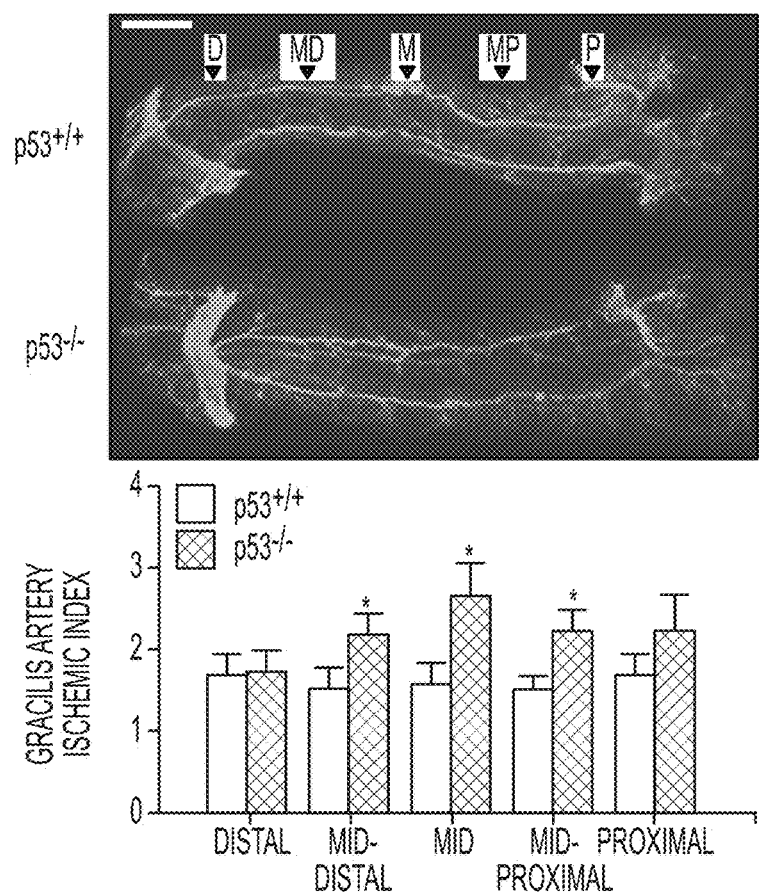
Figure 2B:
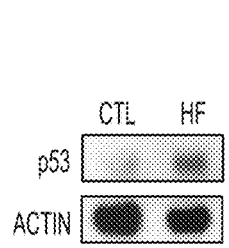
Figure 2C:
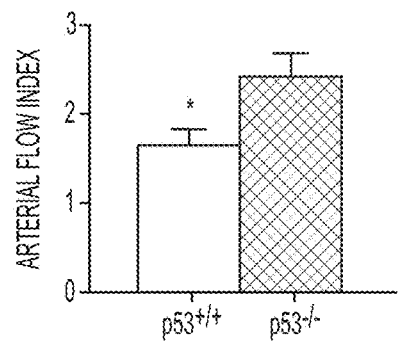
Figure 2D:
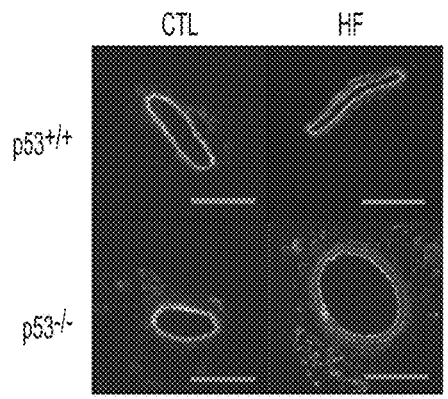
Figure 2D:
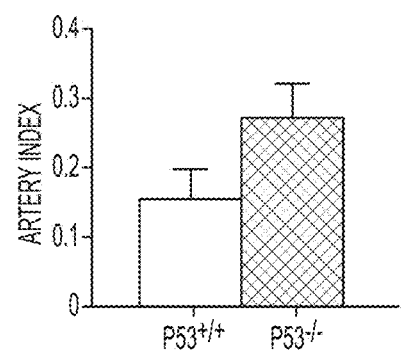

Example 3: Flow Mediated Arterial Enlargement Induces p53, which Suppresses Increased Blood Flow in Collateral Arteries p53 impaired arteriogenesis after ischemia (FIG. 1E and FIG. 1F). FIG. 1E is a bar graph that illustrates artery area. FIG. 1F is a photograph showing gracilis artery ischemic index 2 weeks after hindlimb ischemia. Numerous components of hindlimb ischemia may induce p53, including necrosis, hypoxia and inflammation. To determine whether p53 directly influences flow-mediated arterial enlargement, the expression and effect of p53 was studied in a non-ischemic model of flow-mediated collateral artery formation (mesenteric ligation) (FIG. 2A) [27]. FIG. 2A is a schematic diagram depicting a mesenteric artery ligation model. In $p53^{+/+}$ mice, increased flow in the collateral vessel induced accumulation of the p53 protein as compared to control vessels (FIG. 2B). FIG. 2B is a photograph illustrating an increase in p53 protein expression in high flow arteries 7 days after mesenteric artery ligation. Mice lacking p53 showed a statistically significant increase in blood flow after 2 weeks as compared with $p53^{+/+}$ animals (FIG. 2C), and collateral arteries in mice lacking p53 showed a trend towards increased size at 2 weeks (P=0.1) (FIG. 2D). FIG. 2C is a bar graph representing blood flow restoration two weeks after mesenteric artery ligation in $p53^{-/-}$ mice compared to $p53^{+/+}$ mice. FIG. 2D is a photograph of an improvement in high flow arterial area 2 weeks after mesenteric artery ligation in $p53^{-/-}$ mice.

Example 4: p53 Regulates the HIF-1α/VEGF Pathway, Apoptosis and Endothelial Outgrowth After induction of hindlimb ischemia, $p53^{-/-}$ mice showed increased tissue HIF-1α and VEGF protein levels compared to $p53^{+/+}$ mice (FIG. 3A), indicating that endogenous p53 suppresses the expression of these important angiogenic factors. FIG. 3A is a photograph illustrating loss of p53 in ischemic tissue 3 days after hindlimb ischemia increases HIF-1α and VEGF protein expression. Co-immunoprecipitation of p53 with HIF-1α demonstrated that ischemia induced a direct interaction between the two proteins (FIG. 3B), indicating that ischemia-induced p53 targets HIF-1α for proteasome-mediated degradation as previously reported in vitro [20]. FIG. 3B is a photograph illustrating p53 co-immunoprecipitated with HIF-1α in ischemic tissue following hindlimb ischemia. To further define the angiogenic effect of p53 under isolated conditions, aortic rings from $p53^{+/+}$ and $p53^{-/-}$ mice were embedded in a collagen matrix and subjected to hypoxia to simulate conditions in the ischemic limb. Under hypoxia, $p53^{-/-}$ rings had an increased endothelial outgrowth compared to $p53^{+/+}$ rings (FIG. 3C), indicating that endogenous p53 suppresses hypoxia-induced endothelial cell proliferation and migration, consistent with effects noted in vivo after ischemia. FIG. 3C includes a photograph and bar graph illustrating $p53^{-/-}$ aortic rings subjected to hypoxic conditions demonstrating increased endothelial outgrowth compared to $p53^{+/+}$ aortic rings.

Analysis of apoptosis in ischemic tissue demonstrated that p53$^{-/-}$ mice had significantly fewer apoptotic cells than p53$^{+/+}$ mice (FIG. 3D), indicating that p53 increases apoptosis after ischemia. FIG. 3D includes a photograph and bar graph illustrating loss of p53 resulting in a decrease in detected apoptotic cells in ischemic tissue 3 days after hindlimb ischemia.

Example 5: Pharmacological Augmentation of p53 Impairs Ischemia-Induced Arteriogenesis Treatment of p53$^{+/+}$ mice with the p53 activator quinacrine significantly attenuated the improvement in blood flow after ischemia (FIG. 4A). FIG. 4A is a graph illustrating quinacrine-treated mice showing marked improvement in blood flow restoration compared to vehicle controls 2 weeks after hindlimb ischemia. Morphometric analysis showed that quinacrine treatment did not affect capillary density (FIG. 4B) but did impair collateral development (FIG. 4C). FIG. 4B includes a photograph and bar graph representing quinacrine treatment did not effect capillary density. FIG. 4C is a bar graph illustrating quanacrine treatment did negatively influence larger vessel growth. Moreover, both HIF-1α and VEGF protein levels were suppressed in quinacrine-treated mice (FIG. 4D). FIG. 4D includes a photograph and bar graph illustrating quinacrine-treatment of aortic rings under hypoxic conditions resulting in a significant decrease in endothelial outgrowth compared to vehicle-treated controls. Quinacrine treatment significantly inhibited endothelial outgrowth from aortic rings under hypoxic conditions compared to vehicle-treated controls (FIG. 4E). FIG. 4E is a photograph illustrating ischemic tissue of quinacrine-treated mice revealing decreased expression of HIF-1α and VEGF levels 7 days after hindlimb ischemia. As quinacrine has numerous intracellular targets, we confirmed that the effect of quinacrine on blood flow and arteriogenesis were mediated by activation of p53 by studying its effect in mice lacking p53. Quinacrine treatment had no effect on blood flow after ischemia in p53$^{-/-}$ mice (FIG. 4F) demonstrating that the effects of quinacrine were due to p53 activation. FIG. 4F is a bar graph illustrating quinacrine-treatment in p53 did not affect blood flow restoration by LDPI 2 weeks after hindlimb ischemia.

Figure 5D:
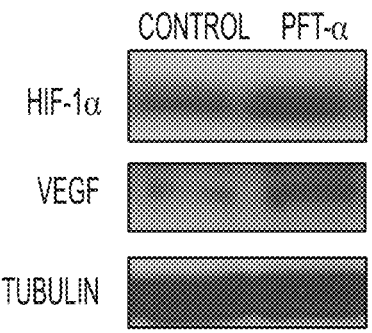
Figure 5E:
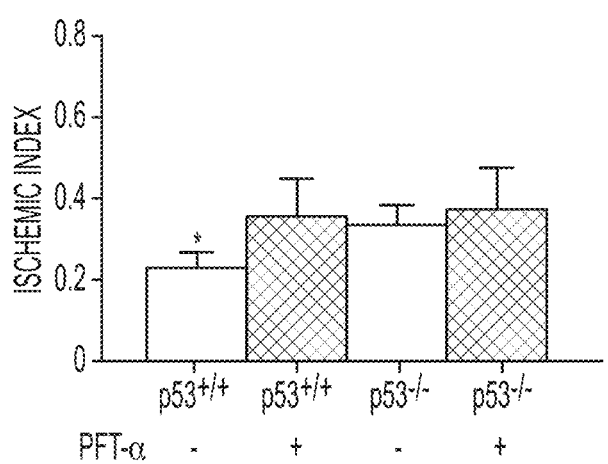

Example 6: Pharmacological Inhibition of p53 Augments Limb Blood Flow and Arteriogenesis Treatment of p53$^{+/+}$ mice with the p53 inhibitor, PFT-α, enhanced blood flow restoration after ischemia compared to vehicle-treated controls (FIG. 5A). FIG. 5A is a bar graph illustrating PFT-α-treated mice demonstrating enhanced blood flow restoration by LDPI 2 weeks after hindlimb ischemia compared to vehicle-treated mice (n=9/group). No difference in capillary growth was detected following PFT-α treatment (FIG. 5B); however, collateral vessel formation increased compared to vehicle-treated controls (FIG. 5C). FIG. 5B is a bar graph illustrating that no statistically significant difference in capillary counts was detected between PFT-α- and vehicle control treated mice (n=3 group). FIG. 5C is a photograph illustrating PFT-α treatment resulting in an increased gracilis artery index 2 weeks after hindlimb ischemia (PFT-α, n=9; vehicle-control, n=7). PFT-α was associated with an increase in both HIF-1α and VEGF protein levels in ischemic tissue 3 days after surgery (FIG. 5D). FIG. 5D is a photograph illustrating PFT-α-treated animals demonstrating enhanced expression of HIF-1α and VEGF protein levels 3 days after surgery (n=2/group). Again the specificity of PFT-α for the p53 pathway was examined by studying its effect in mice lacking p53. Treatment of p53$^{-/-}$ mice with PFT-α had no effect on blood flow restoration after ischemia (FIG. 5E), demonstrating that the beneficial effects of PFT-α on blood flow and arteriogenesis were due to inhibition of p53. FIG. 5E is a bar graph illustrating treatment of p53$^{-/-}$ mice with PFT-α did not affect blood flow by LDPI 2 weeks after hindlimb ischemia (n=4/group). Day 14 time-point of PFT-α- and vehicle control-treated mice from panel A added to panel D for direct comparison. C) Magnification 20×. Data presented as mean±s.e.m.*p<0.05. [Scale bar: 1 mm (C); magnification 20× (C)].

REFERENCES

1. Schaper W, Buschmann I (1999) Arteriogenesis, the good and bad of it. Cardiovascular research 43: 835-837.
2. Wang G L, Jiang B H, Rue E A, Semenza G L (1995) Hypoxia-inducible factor 1 is a basic-helix-loop-helix-PAS heterodimer regulated by cellular 02 tension. Proceedings of the National Academy of Sciences of the United States of America 92: 5510-5514.
3. Jung F, Palmer L A, Zhou N, Johns R A (2000) Hypoxic regulation of inducible nitric oxide synthase via hypoxia inducible factor-1 in cardiac myocytes. Circulation research 86: 319-325.
4. Forsythe J A, Jiang B H, Iyer N V, Agani F, Leung S W, et al. (1996) Activation of vascular endothelial growth factor gene transcription by hypoxia-inducible factor 1. Molecular and cellular biology 16: 4604-4613.
5. Lee J G, Dahi S, Mahimkar R, Tulloch N L, Alfonso-Jaume M A, et al. (2005) Intronic regulation of matrix metalloproteinase-2 revealed by in vivo transcriptional analysis in ischemia. Proceedings of the National Academy of Sciences of the United States of America 102: 16345-16350.
6. Semenza G L (2003) Targeting HIF-1 for cancer therapy. Nature reviews Cancer 3: 721-732.
7. Ziegler-Graham K, MacKenzie E J, Ephraim P L, Travison T G, Brookmeyer R (2008) Estimating the prevalence of limb loss in the United States: 2005 to 2050. Archives of physical medicine and rehabilitation 89: 422-429.
8. Giaccia A J, Kastan M B (1998) The complexity of p53 modulation: emerging patterns from divergent signals. Genes & development 12: 2973-2983.
9. Graeber T G, Osmanian C, Jacks T, Housman D E, Koch C J, et al. (1996) Hypoxia-mediated selection of cells with diminished apoptotic potential in solid tumours. Nature 379: 88-91.
10. Graeber T G, Peterson J F, Tsai M, Monica K, Fornace A J, Jr., et al. (1994) Hypoxia induces accumulation of p53 protein, but activation of a G1-phase checkpoint by low-oxygen conditions is independent of p53 status. Molecular and cellular biology 14: 6264-6277.
11. Levine A J (1997) p53, the cellular gatekeeper for growth and division. Cell 88: 323-331.
12. Teodoro J G, Evans S K, Green M R (2007) Inhibition of tumor angiogenesis by p53: a new role for the guardian of the genome. Journal of molecular medicine 85: 1175-1186.
13. Sano M, Minamino T, Toko H, Miyauchi H, Orimo M, et al. (2007) p53-induced inhibition of Hif-1 causes cardiac dysfunction during pressure overload. Nature 446: 444-448.

14. Kieser A, Weich H A, Brandner G, Marme D, Kolch W (1994) Mutant p53 potentiates protein kinase C induction of vascular endothelial growth factor expression. Oncogene 9: 963-969.
15. Galy B, Creancier L, Zanibellato C, Prats A C, Prats H (2001) Tumour suppressor p53 inhibits human fibroblast growth factor 2 expression by a post-transcriptional mechanism. Oncogene 20: 1669-1677.
16. Moriya J, Minamino T, Tateno K, Okada S, Uemura A, et al. (2010) Inhibition of semaphorin as a novel strategy for therapeutic angiogenesis. Circulation research 106: 391-398.
17. Dameron K M, Volpert O V, Tainsky M A, Bouck N (1994) The p53 tumor suppressor gene inhibits angiogenesis by stimulating the production of thrombospondin. Cold Spring Harbor symposia on quantitative biology 59: 483-489.
18. Assadian S, El-Assaad W, Wang X Q, Gannon P O, Barres V, et al. (2012) p53 inhibits angiogenesis by inducing the production of Arresten. Cancer research 72: 1270-1279.
19. Teodoro J G, Parker A E, Zhu X, Green M R (2006) p53-mediated inhibition of angiogenesis through up-regulation of a collagen prolyl hydroxylase. Science 313: 968-971.
20. Ravi R, Mookerjee B, Bhujwalla Z M, Sutter C H, Artemov D, et al. (2000) Regulation of tumor angiogenesis by p53-induced degradation of hypoxia-inducible factor 1alpha. Genes & development 14: 34-44.
21. Sata M, Tanaka K, Ishizaka N, Hirata Y, Nagai R (2003) Absence of p53 leads to accelerated neointimal hyperplasia after vascular injury. Arteriosclerosis, thrombosis, and vascular biology 23: 1548-1552.
22. Mercer J, Bennett M (2006) The role of p53 in atherosclerosis. Cell cycle 5: 1907-1909.
23. Cheng J, Cui R, Chen C H, Du J (2007) Oxidized low-density lipoprotein stimulates p53-dependent activation of proapoptotic Bax leading to apoptosis of differentiated endothelial progenitor cells. Endocrinology 148: 2085-2094.
24. Morimoto Y, Bando Y K, Shigeta T, Monji A, Murohara T (2011) Atorvastatin prevents ischemic limb loss in type 2 diabetes: role of p53. Journal of atherosclerosis and thrombosis 18: 200-208.
25. Nguyen P D, Tutela J P, Thanik V D, Knobel D, Allen R J, Jr., et al. (2010) Improved diabetic wound healing through topical silencing of p53 is associated with augmented vasculogenic mediators. Wound repair and regeneration: official publication of the Wound Healing Society [and] the European Tissue Repair Society 18: 553-559.
26. Chavala S H, Kim Y, Tudisco L, Cicatiello V, Milde T, et al. (2013) Retinal angiogenesis suppression through small molecule activation of p53. The Journal of clinical investigation 123: 4170-4181.
27. Unthank J L, Fath S W, Burkhart H M, Miller S C, Dalsing M C (1996) Wall remodeling during luminal expansion of mesenteric arterial collaterals in the rat. Circulation research 79: 1015-1023.
28. Paek R, Chang D S, Brevetti L S, Rollins M D, Brady S, et al. (2002) Correlation of a simple direct measurement of muscle pO(2) to a clinical ischemia index and histology in a rat model of chronic severe hindlimb ischemia. Journal of vascular surgery 36: 172-179.
29. Gudkov A V, Komarova E A (2010) Pathologies associated with the p53 response. Cold Spring Harbor perspectives in biology 2: a001180.
30. Heil M, Eitenmuller I, Schmitz-Rixen T, Schaper W (2006) Arteriogenesis versus angiogenesis: similarities and differences. Journal of cellular and molecular medicine 10: 45-55.
31. Mukhopadhyay U K, Eves R, Jia L, Mooney P, Mak A S (2009) p53 suppresses Src-induced podosome and rosette formation and cellular invasiveness through the upregulation of caldesmon. Molecular and cellular biology 29: 3088-3098.
32. Schmid T, Zhou J, Kohl R, Brune B (2004) p300 relieves p53-evoked transcriptional repression of hypoxia-inducible factor-1 (HIF-1). The Biochemical journal 380: 289-295.
33. Zhang L, Yu D, Hu M, Xiong S, Lang A, et al. (2000) Wild-type p53 suppresses angiogenesis in human leiomyosarcoma and synovial sarcoma by transcriptional suppression of vascular endothelial growth factor expression. Cancer research 60: 3655-3661.
34. Yamakuchi M, Lotterman C D, Bao C, Hruban R H, Karim B, et al. (2010) P53-induced microRNA-107 inhibits HIF-1 and tumor angiogenesis. Proceedings of the National Academy of Sciences of the United States of America 107: 6334-6339.
35. Favata M F, Horiuchi K Y, Manos E J, Daulerio A J, Stradley D A, et al. (1998) Identification of a novel inhibitor of mitogen-activated protein kinase kinase. The Journal of biological chemistry 273: 18623-18632.
36. Liu P, Xu B, Cavalieri T A, Hock C E (2006) Pifithrin-alpha attenuates p53-mediated apoptosis and improves cardiac function in response to myocardial ischemia/reperfusion in aged rats. Shock 26: 608-614.
37. Matsusaka H, Ide T, Matsushima S, Ikeuchi M, Kubota T, et al. (2006) Targeted deletion of p53 prevents cardiac rupture after myocardial infarction in mice. Cardiovascular research 70: 457-465.
38. Zhang Y, Kohler K, Xu J, Lu D, Braun T, et al. (2011) Inhibition of p53 after acute myocardial infarction: reduction of apoptosis is counteracted by disturbed scar formation and cardiac rupture. Journal of molecular and cellular cardiology 50: 471-478.
39. Abaci A, Oguzhan A, Kahraman S, Eryol N K, Unal S, et al. (1999) Effect of diabetes mellitus on formation of coronary collateral vessels. Circulation 99: 2239-2242.
40. Loomans C J, De Koning E J, Staal F J, Rabelink T J, Zonneveld A J (2005) Endothelial progenitor cell dysfunction in type 1 diabetes: another consequence of oxidative stress? Antioxidants & redox signaling 7: 1468-1475.

What is claimed is:

1. A method for treating diabetic-induced ischemia in a subject in need thereof comprising locally administering a therapeutically effective amount of the p53 inhibitor pifithrin-α (2-Amino-3-[2-4-methylphenyl-2-oxoethyl]-2,3,4,5,6,7-hexahydro-1,3-benzothiazol-2-ylium bromide) to a site of ischemic tissue in the subject, wherein the site of ischemic tissue is in a limb.

2. The method of claim 1 wherein the subject is human.

3. The method of claim 1 wherein local administration is performed by a route selected from the group consisting of limb perfusion, intravenous, intraarterial, intramuscular, and intraarticular.

4. The method of claim 1 wherein the p53 inhibitor pifithrin-α (2-Amino-3-[2-4-methylphenyl-2-oxoethyl]-2,3,4,5,6,7-hexahydro-1,3-benzothiazol-2-ylium bromide) is administered alone or in conjunction with bypass surgery, endovascular surgery, or endovascular revascularization.

5. A method for treating diabetic-induced ischemia in a subject in need thereof comprising locally administering a therapeutically effective amount of the p53 inhibitor pifithrin-α (2-Amino-3-[2-4-methylphenyl-2-oxoethyl]-2,3,4,5,6,7-hexahydro-1,3-benzothiazol-2-ylium bromide) to a site of ischemic tissue in the subject, wherein the p53 inhibitor is locally administered, and further administering one or more therapeutic agents.

6. The method of claim 5 wherein the therapeutic agent is selected from the group consisting of insulin, exenatide, liraglutide, pramlintide, one or more sulfonylurea, metformin, one or more alpha glucosidase inhibitor, one or more thiazolidinedione, and any combination thereof.

7. The method of claim 6, wherein the sulfonylurea is selected from glyburide, glimepiride, and glipizide, the alpha glucosidase inhibitor is selected from acarbose, miglitol, and voglibose, and the thiazolidinedione is selected from pioglitazone and rosiglitazone.

8. A method for treating diabetic-induced ischemia in a subject in need thereof comprising locally administering a therapeutically effective amount of the p53 inhibitor pifithrin-α (2-Amino-3-[2-4-methylphenyl-2-oxoethyl]-2,3,4,5,6,7-hexahydro-1,3-benzothiazol-2-ylium bromide) to a site of ischemic tissue in the subject, and further comprising administering the p53 inhibitor pifithrin-α (2-Amino-3-[2-4-methylphenyl-2-oxoethyl]-2,3,4,5,6,7-hexahydro-1,3-benzothiazol-2-ylium bromide) orally, parenterally, sublingually, transdermally, rectally, transmucosally, or topically via a gel.

9. The method of claim 8 wherein parenteral administration is intravenous, intraarterial, intraperitoneal, intramuscular, intrathecal, or intraarticular administration.

10. The method of claim 9 wherein the p53 inhibitor pifithrin-α (2-Amino-3-[2-4-methylphenyl-2-oxoethyl]-2,3,4,5,6,7-hexahydro-1,3-benzothiazol-2-ylium bromide) is administered in combination with a catheter delivery system to allow targeted delivery into a specific focal anatomic location or arterial bed.

11. The method of claim 8 wherein the p53 inhibitor pifithrin-α (2-Amino-3-[2-4-methylphenyl-2-oxoethyl]-2,3,4,5,6,7-hexahydro-1,3-benzothiazol-2-ylium bromide) is administered using a topical gel to allow controlled release over a prolonged period of time.

12. The method of claim 8 wherein the p53 inhibitor pifithrin-α (2-Amino-3-[2-4-methylphenyl-2-oxoethyl]-2,3,4,5,6,7-hexahydro-1,3-benzothiazol-2-ylium bromide) is administered using a nanoparticle formulation to allow effective transmucosal absorption.

13. The method of claim 8 wherein the p53 inhibitor pifithrin-α (2-Amino-3-[2-4-methylphenyl-2-oxoethyl]-2,3,4,5,6,7-hexahydro-1,3-benzothiazol-2-ylium bromide) is administered in a dose of from about 25 mg to 250 mg.

14. A method of improving limb perfusion in a subject in need thereof comprising locally administering a therapeutically effective amount of the p53 inhibitor pifithrin-α (2-Amino-3-[2-4-methylphenyl-2-oxoethyl]-2,3,4,5,6,7-hexahydro-1,3-benzothiazol-2-ylium bromide) to cells of a limb of a subject in need thereof, and optionally further administering another therapeutic agent.

15. The method of claim 14 wherein the therapeutic agent is selected from the group consisting of insulin, exenatide, liraglutide, pramlintide, one or more sulfonylurea, metformin, one or more alpha glucosidase inhibitor, one or more thiazolidinedione, and any combination thereof.

16. The method of claim 14 wherein the subject is human.

17. The method of claim 14 wherein the therapeutic agent is selected from the group consisting of simvastatin, pravastatin, lovastatin, atorvastatin, niacin, rosuvastatin, pitavastatin, fluvastatin, and any combination thereof.

18. A method of improving ischemia-induced angiogenesis in tissue of a limb comprising administering a therapeutically effective amount of the p53 inhibitor pifithrin-α (2-Amino-3-[2-4-methylphenyl-2-oxoethyl]-2,3,4,5,6,7-hexahydro-1,3-benzothiazol-2-ylium bromide) to a subject in need thereof, and optionally further administering another therapeutic agent.

19. The method of claim 18 wherein the subject is human.

20. The method of claim 18 wherein the therapeutic agent is selected from the group consisting of insulin, exenatide, liraglutide, pramlintide, one or more sulfonylurea, metformin, one or more alpha glucosidase inhibitor, one or more thiazolidinedione, and any combination thereof.

21. The method of claim 20, wherein the sulfonylurea is selected from glyburide, glimepiride, and glipizide, the alpha glucosidase inhibitor is selected from acarbose, miglitol, and voglibose, and the thiazolidinedione is selected from pioglitazone and rosiglitazone.

22. The method of claim 18 wherein the therapeutic agent is selected from the group consisting of simvastatin, pravastatin, lovastatin, atorvastatin, niacin, rosuvastatin, pitavastatin, fluvastatin, and any combination thereof.

23. A method of improving ischemia-induced arteriogenesis in tissue of a limb comprising administering a therapeutically effective amount of the p53 inhibitor pifithrin-α (2-Amino-3-[2-4-methylphenyl-2-oxoethyl]-2,3,4,5,6,7-hexahydro-1,3-benzothiazol-2-ylium bromide) to the limb of a subject in need thereof, and optionally further administering another therapeutic agent.

24. The method of claim 23 wherein the subject is human.

25. The method of claim 23 wherein the therapeutic agent is selected from the group consisting of insulin, exenatide, liraglutide, pramlintide, one or more sulfonylurea, metformin, one or more alpha glucosidase inhibitor, one or more thiazolidinedione, and any combination thereof.

26. The method of claim 25, wherein the sulfonylurea is selected from glyburide, glimepiride, and glipizide, the alpha glucosidase inhibitor is selected from acarbose, miglitol, and voglibose, and the thiazolidinedione is selected from pioglitazone and rosiglitazone.

27. The method of claim 23 wherein the therapeutic agent is selected from the group consisting of simvastatin, pravastatin, lovastatin, atorvastatin, niacin, rosuvastatin, pitavastatin, fluvastatin, and any combination thereof.

* * * * *